United States Patent
Schaller et al.

(10) Patent No.: US 11,052,930 B2
(45) Date of Patent: Jul. 6, 2021

(54) ROBOTIC ARM CART HAVING LOCKING SWIVEL JOINTS AND OTHER POSITION ADJUSTMENT FEATURES AND USES THEREFOR

(71) Applicant: Verb Surgical Inc., Mountain View, CA (US)

(72) Inventors: Michael P. Schaller, Redwood City, CA (US); Brendan C. Reese, San Francisco, CA (US); Luke W. Clauson, Reno, NV (US)

(73) Assignee: Verb Surgical Inc., Santa Clara, CA (US)

( * ) Notice: Subject to any disclaimer, the term of this patent is extended or adjusted under 35 U.S.C. 154(b) by 868 days.

(21) Appl. No.: 15/788,730

(22) Filed: Oct. 19, 2017

(65) Prior Publication Data

US 2018/0362060 A1 Dec. 20, 2018

Related U.S. Application Data

(60) Provisional application No. 62/520,986, filed on Jun. 16, 2017.

(51) Int. Cl.
*A61B 34/30* (2016.01)
*B62B 3/10* (2006.01)
(Continued)

(52) U.S. Cl.
CPC ............... *B62B 3/10* (2013.01); *A61B 34/30* (2016.02); *A61B 90/50* (2016.02); *A61B 90/57* (2016.02);
(Continued)

(58) Field of Classification Search
CPC .. A61G 13/101; A61G 13/105; A61G 13/129; A61G 13/1285; A61B 2090/571;
(Continued)

(56) References Cited

U.S. PATENT DOCUMENTS 6,246,200 B1 6/2001 Blumenkranz et al.
10,333,296 B1 * 6/2019 Wu .................. H02J 50/90
(Continued)

FOREIGN PATENT DOCUMENTS

EP 1190680 A1 3/2002
EP 2145586 A1 1/2010
(Continued)

OTHER PUBLICATIONS

International Preliminary Report on Patentability for International Application No. PCT/US2018/035509 dated Dec. 26, 2019, 6 pages.
(Continued)

*Primary Examiner* — Daniel J Wiley
(74) *Attorney, Agent, or Firm* — Womble Bond Dickinson (US) LLP

(57) ABSTRACT

Apparatuses and methods described herein relate to arm carts for transporting and securing a robotic arm to a surgical table. In some embodiments, an arm cart may include an arm support having two joints that can be manipulated to move an arm into a position in which a coupler of the arm is engageable with a coupling site of a surgical table. In some embodiments, an arm cart may include an arm support that is rotatable and translatable to permit movement of an attachment area for receiving and attaching a coupling site of a surgical table to a coupler attached to an arm. In some embodiments, an arm cart may include an arm support that releasably couples to a middle segment of the arm positioned at least two segments away from an end of the arm having a coupler for coupling to a coupling site of a surgical table.

17 Claims, 22 Drawing Sheets

(51) Int. Cl.
  *B25J 18/00* (2006.01)
  *B62B 3/02* (2006.01)
  *B62B 3/04* (2006.01)
  *A61G 13/10* (2006.01)
  *A61B 90/57* (2016.01)
  *A61B 90/50* (2016.01)
  *A61B 17/00* (2006.01)

(52) U.S. Cl.
  CPC ............ *A61G 13/101* (2013.01); *B25J 18/00* (2013.01); *B62B 3/02* (2013.01); *B62B 3/04* (2013.01); *A61B 2017/00477* (2013.01); *A61B 2090/504* (2016.02); *A61B 2090/508* (2016.02); *A61B 2090/571* (2016.02); *A61G 2203/80* (2013.01); *B62B 2202/48* (2013.01); *B62B 2203/60* (2013.01); *B62B 2203/70* (2013.01)

(58) Field of Classification Search
  CPC ........ A61B 90/50; A61B 34/30; A61B 90/57; A61B 90/60; B62B 3/02; B62B 3/04
  See application file for complete search history.

(56) References Cited

U.S. PATENT DOCUMENTS

| | | |
|---|---|---|
| 2002/0133174 A1 | 9/2002 | Charles et al. |
| 2015/0374446 A1 | 12/2015 | Malackowski et al. |
| 2017/0065355 A1 | 9/2017 | Ross et al. |
| 2018/0296299 A1* | 10/2018 | Iceman .................. A61B 34/35 |
| 2018/0333215 A1* | 11/2018 | Timm .................... A61B 90/57 |

FOREIGN PATENT DOCUMENTS

| | | |
|---|---|---|
| EP | 2893898 A1 | 7/2015 |
| JP | 2002-165804 A | 6/2002 |
| JP | 2002-325361 A | 11/2002 |
| JP | 2014-180489 A | 9/2014 |
| JP | 2016-105802 A | 6/2016 |
| JP | 2017-513550 A | 6/2017 |
| WO | 2016/048738 A1 | 3/2016 |
| WO | WO2017083453 A1 | 5/2017 |

OTHER PUBLICATIONS

Australian Examination Report for Australian Application No. 2018285614 dated Feb. 14, 2020, 3 pages.
PCT Search Report and Written Opinion dated Sep. 13, 2018, for related PCT Appln. No. PCUS2018/035509 7 Pages.
Notice of Acceptance of the Australian Patent Office dated May 25, 2020 for related Australian Patent Application No. 2018285614.
Notice of Reasons for Rejection of the Japanese Patent Office dated Nov. 4, 2020 for related Japanese Patent Application No. 2019-560685.
Supplementary European Search Report and Search Opinion of the European Patent Office dated Feb. 23, 2021 for related European Patent Application No. 18817093.0.
Examination Search Report of the Canadian Patent Office dated Mar. 11, 2021 for related Canadian Patent Application No. 3061171.

* cited by examiner

ROBOTIC ARM CART HAVING LOCKING SWIVEL JOINTS AND OTHER POSITION ADJUSTMENT FEATURES AND USES THEREFOR

CROSS-REFERENCE TO RELATED APPLICATIONS

This application claims priority to U.S. patent application Ser. No. 62/520,986, filed on Jun. 16, 2017, which is hereby incorporated by reference in its entirety.

BACKGROUND

Embodiments described herein relate to apparatuses and methods for a robotic arm cart for transporting, delivering, and securing robotic arms to, for example, a surgical table.

In surgical robotic systems, robotic arms may be coupled to a patient operating table. Once coupled, the robotic arms may assist with manipulating instruments based on commands from an operator. For example, in response to operator commands, a robotic arm having multiple degrees of freedom may move a surgical instrument in order to perform an operation on a patient. In many conventional robotic systems, however, robotic arms may be difficult to attach and remove from a surgical operating table. Some conventional robotic arms require a technician having specialized training to connect and disconnect the robotic arms to the table such that changing or servicing a robotic arm is a time-consuming and expensive task. Many robotic arms may also be heavy and difficult to transport to a surgical site, further adding to problems associated with their storage, attachment, and removal. During a coupling operation, it may also be difficult for a technician to align a coupling portion of the robotic arm with a receiving site on a surgical table. The technician may need to support the robotic arm and manipulate its coupling end in order to place the coupling end into the receiving site on the surgical table. Depending on the dimensions, weight, and adjustability of the robotic arm, the process of attaching the robotic arm to the surgical table may require significant physical effort and time, increasing the risk of accidental damage to the robotic arm.

Removal and reattachment of a robotic arm may also introduce misalignment between the robotic arm and surgical table. Furthermore, some conventional robotic arm coupling mechanisms use removable components (e.g., bolts) that may be misplaced and result in misalignment or failure of an arm to table coupling. Additional apparatuses and methods for coupling a robotic arm to a surgical table are desirable.

SUMMARY

Apparatuses and methods for providing a robotic arm cart for transporting, delivering, and securing robotic arms to a surgical table having a table top on which a patient can be disposed are described herein. In some embodiments, a robotic arm cart having an arm support with one or more swivel joints may be provided. The cart may have a base that is freely movable between a first location remote from a surgical table and a second location adjacent to the surgical table. The arm support of the cart may be coupled to the base and releasably coupled to a robotic arm. The arm support may include one or more members that are coupled to each other via swivel joints. These members may be movable relative to each other via the swivel joints. The arm support may also include locking mechanisms for locking and unlocking the swivel joints. When unlocked, the swivel joints may move the arm from a first position in which the arm is not engageable with a coupling site of the surgical table to a second position in which the arm is engageable with the coupling site.

In some embodiments, a method of coupling a robotic arm to a surgical table may include moving a robotic arm cart from a first location remote from the surgical table to a second location proximate to the surgical table, and manipulating an arm support of the cart to move the surgical arm such that a coupler of the surgical arm can be engaged with a coupling site of a surgical table. Manipulating the arm support of the cart may include unlocking one or more swivel joints of the arm support and rotating different members of the arm support to place the coupler of the arm support in alignment with the coupling site of the surgical table such that the coupler can be releasably coupled to the coupling site.

In some embodiments, a robotic arm cart including an arm support that is rotatable and translatable may be provided. The cart may have a base that is freely movable between a first location remote from a surgical table and a second location adjacent to the surgical table. The attachment device may define an attachment area for receiving a coupling site of the surgical table as well as a coupler attached to the robotic arm. The arm support may be rotatable and translatable to permit movement of the attachment area such that the coupling site can be directed into the attachment area. The coupler may have a first engagement member for releasably engaging with the arm support and a second engagement member for releasably engaging with the coupling site of the surgical table. The coupler may also have an actuator that engages and disengages the first and second engagement members from the arm support and the coupling site, respectively.

In some embodiments, a method of coupling a robotic arm to a surgical table may include moving a robotic arm cart from a first location remote from the surgical table to a second location proximate to the surgical table, translating or rotating an arm support of the cart such that a coupling site of the surgical table can be inserted into an attachment area of the arm support, inserting the coupling site into the attachment area, lowering a coupler attached to the arm into the attachment area such that the coupler is placed over the coupling site, and engaging the coupler to the coupling site. The coupler may be engaged to the cart during transport and alignment of the coupling site with the attachment area but can be disengaged from the cart when the coupler is placed over and engaged to the coupling site.

In some embodiments, a robotic arm cart including an arm support that is designed to couple to a middle segment of a robotic arm. The arm may include at least five segments connected in serial to one another via a plurality of joints. One end of the arm may include a coupler for coupling to a coupling site of a surgical table. The arm support may be coupled to a middle segment of the arm that is positioned at least two segments away from the first end of the arm such that at least two joints are disposed between the middle segment and the first end of the arm. The segments of the arm may be movable to enable the coupler to be aligned with the coupling site for engagement to the coupling site.

BRIEF DESCRIPTION OF THE DRAWINGS

FIGS. 18, 19, 20, and 21 illustrate the arm cart in operation.

DETAILED DESCRIPTION

Apparatuses and methods for providing a robotic arm cart for transporting, delivering, and securing robotic arms to a surgical table having a table top on which a patient can be disposed are described herein. These apparatuses and methods may enable an operator to quickly align and couple a robotic arm to a surgical table.

In some embodiments, an apparatus includes an arm cart including an arm container and a base. The arm container can be configured to receive and contain one or more robotic arms. The arm cart can include a first coupling member configured to engage with a second coupling member associated with a surgical table such that, when the first coupling member is engaged with the second coupling member, the one or more robotic arms can be releasably coupled with the surgical table. The arm cart can provide for movement of the one or more robotic arms in at least one of a lateral, longitudinal, or vertical direction relative to the table top prior to the securement of the one or more robotic arms to the surgical table.

Figure 1A:
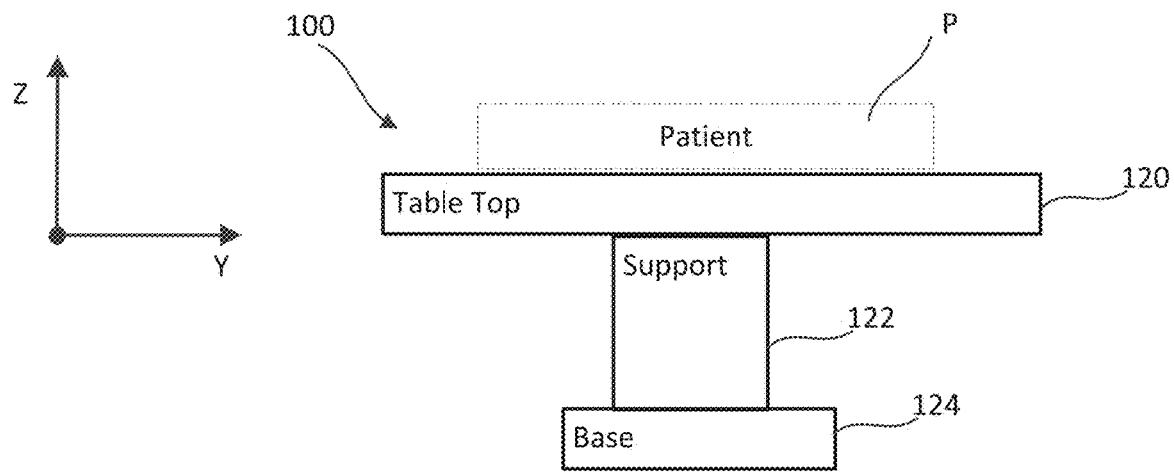
FIGS. 1A and 1B are a schematic side view and a schematic top view, respectively, of a surgical table, according to an embodiment.
Figure 1B:
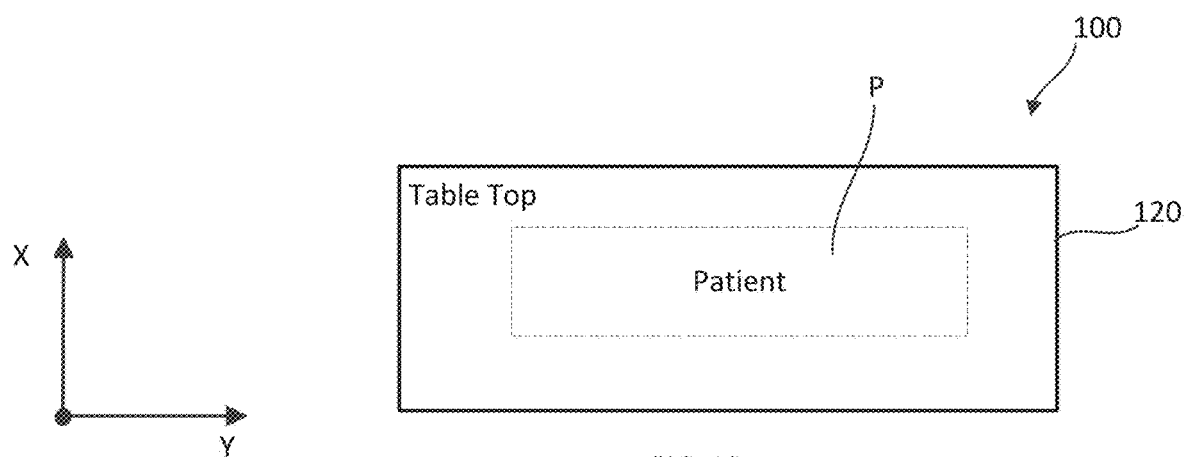

As shown schematically in FIGS. 1A-1B, a surgical table 100 includes a table top 120, a table support 122 and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axes. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
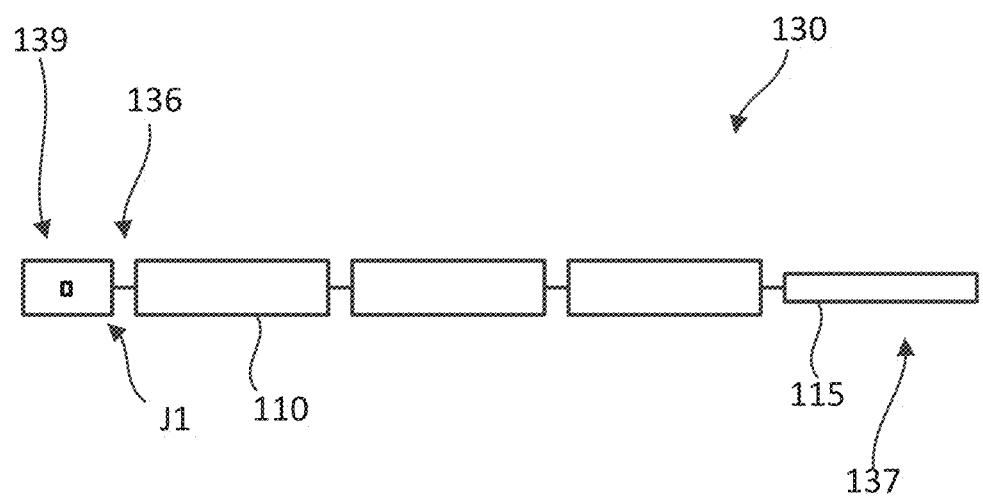
FIG. 1C is a schematic side view of a robotic arm, according to an embodiment, shown in an extended or use configuration.
Figure 1D:
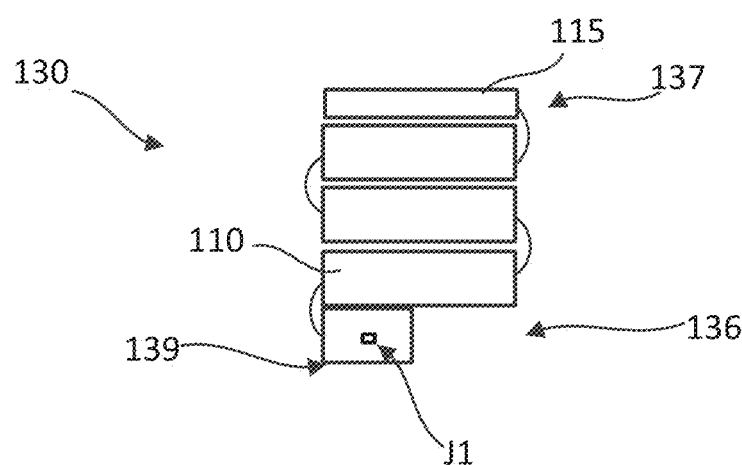
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139 (also referred to as a coupler herein). The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can provide a pivot joint to allow a distal segment of the robotic arm 130 to pivot relative to the table 100. The robotic arm 130 can be moved between various extended configurations for use during a surgical procedure, as shown in FIG. 1C, and various folded or collapsed configurations for storage when not in use, as shown in FIG. 1D.

FIGS. 2A-22 illustrate various embodiments describing apparatuses and methods for transporting, delivering, and securing a robotic arm to a surgical table. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. In some embodiments, the robotic arms 230 can be permanently or releasably coupled, in a fixed or movable location, to an arm adapter that is coupled to or separate from the surgical table. For example, as shown schematically in FIG. 2B, an arm adapter 246 can be coupled to or separate from but engageable with or couplable to the table top 220. The robotic arms 230 can be coupled to the arm adapter 246.

Figure 2A:
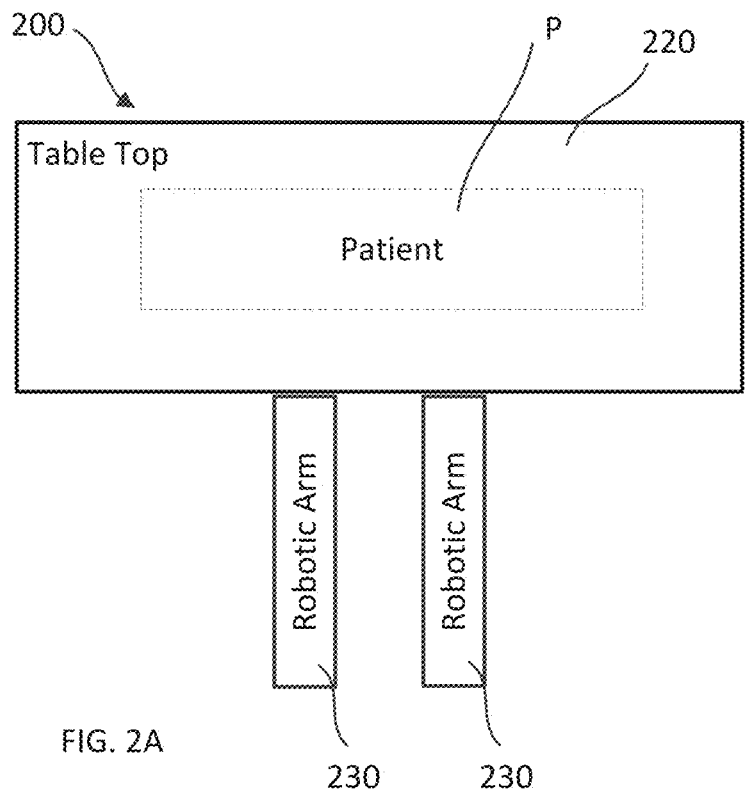
FIG. 2A is a schematic top view of a surgical table with robotic arms coupled thereto, according to an embodiment.
Figure 2B:
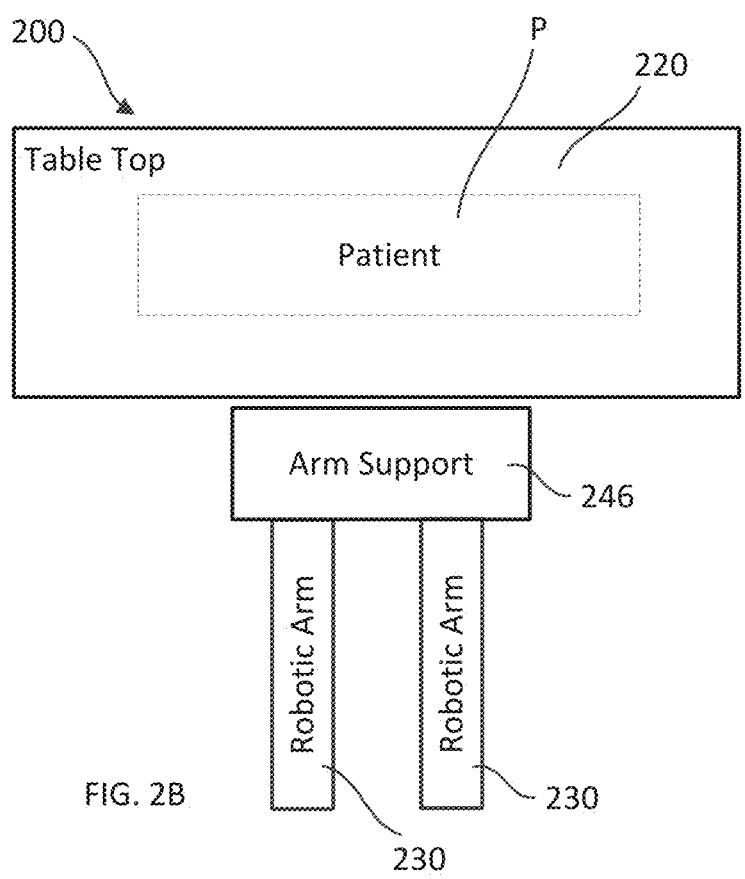
FIG. 2B is a schematic top view of a surgical table with robotic arms and an arm adapter coupled thereto, according to an embodiment.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. As shown schematically in FIG. 3, an arm cart 350 can be configured to support one or more robotic arms. The arm cart 350 includes a first robotic arm 330A and can include an optional second robotic arm 330B. Although two robotic arms 330A, 330B are shown, the arm cart 350 can be configured to contain, transport, and/or deliver any suitable number of robotic arms, such as, for example, one robotic arm, three robotic arms, or four robotic arms.

The arm cart 350 can support the first robotic arm 330A (and the optional second robotic arm 330B) in a variety of configurations. In some embodiments, the arm cart 350 can support the robotic arm 330A such that the center of gravity of the robotic arm 330A is below one or more support structure locations (e.g., cradles) of the arm cart 350 such that the stability of the robotic arm 330A and the arm cart 350 is increased. In some embodiments, the arm cart 350 can support the robotic arm 330A such that the arm cart 350 bears most or all of the weight of the robotic arm 330A and a coupling mechanism (not shown) of the robotic arm 330A can be manually manipulated by a user without the user bearing the most or all of the weight of the robotic arm. For example, the robotic arm 330A can be suspended from a structure of the arm cart 350 or rested on a structure of the arm cart 350. In some embodiments, the arm cart 350 can be configured to secure the robotic arm 330A to the arm cart 350.

The arm cart 350 can be configured for movement such as, for example, by including wheels. The arm cart 350 can be configured to protect the robotic arm 330A from potential impact with the surrounding of the arm cart 350 during, for example, transport or storage. In some embodiments, the arm cart 350 can be configured to move the robotic arm 330A between one or more positions and/or one or more orientations, including, for example, a folded storage or transport position and a deployed or coupling position.

The arm cart 350 can include an arm container 352 and a base 354. The arm container 352 is configured to support, protect, and promote sterility for one or more robotic arms (e.g., the first robotic arm 330A and the optional second robotic arm 330B) during transportation of the robotic arms, for example, from a storage area to the operating area, and during transfer of the one or more robotic arms from the arm cart 350 to a surgical table (e.g., the surgical table 100 and/or the surgical table 200) for use during the surgical procedure. While the one or more robotic arms 330A, 330B are stored and/or transported by the arm cart 350, the one or more robotic arms 330A, 330B can be mostly, substantially completely, or completely maintained within the footprint of the arm cart 350 such that the one or more robotic arms 330A, 330B will be less likely to be accidentally bumped or damaged. In some embodiments, the arm container 352 can be structured as a vertically-extending protection frame that, in combination with the base 354, defines a space for storing the one or more robotic arms 330A, 330B. In some embodiments, when the one or more robotic arms 330A, 330B are stored within the arm cart 350, the robotic arms 330A, 330B can be maintained within the perimeter of the base 354, but may extend beyond the perimeter of the arm container 352.

The arm container 352 can be further configured to facilitate safe, efficient, sterile, and repeatable transfer of the one or more robotic arms 330A, 330B to the surgical table and/or an arm adapter. In some embodiments, transfer of the one or more robotic arms 330A, 330B from the arm cart 350 to the surgical table can be performed manually.

The base 354 can be configured to support the arm container 352 and provide transportation of the arm cart 350 to the surgical area. The base 354 can include any suitable means for movement of the arm cart 350 relative to the floor. For example, the base 354 can include wheels such that a medical provider can push/pull the arm cart to/from the operating area.

The arm cart 350 can include features that assist in aligning the one or more robotic arms 330A, 330B for transfer to the surgical table along the X, Y, and/or Z axes and/or rotationally about the X, Y, and/or Z axes. For example, as described above, the base 354 can include any suitable means for movement of the arm cart 350 such that the arm cart 350 can be moved along the X axis and/or the Y axis relative to the surgical table. Additionally, the arm cart 350 can include any suitable means for adjusting the height of the arm cart 350 and/or the one or more robotic arms 330A, 330B such that the height of the one or more robotic arms 330A, 330B can be adjusted relative to the surgical table. Thus, the arm cart 350 can move the one or more robotic arms 330A, 330B along the X, Y, and/or Z axes and/or rotationally about the X, Y, and/or Z axes such that a coupling portion of at least one of the one or more robotic arms 330A, 330B can be aligned for engagement with a mating coupling portion on a table or a table adapter.

In some embodiments, the arm cart 350 houses the one or more robotic arms 330A, 330B such that a line of sight can be maintained from the operator of the arm cart 350 to the portion of the surgical table to which the one or more robotic arms 330A, 330B are to be transferred during the approach of the arm cart 350 to the surgical table and the transfer of the one or more robotic arms 330A, 330B to the surgical table.

Figure 3:
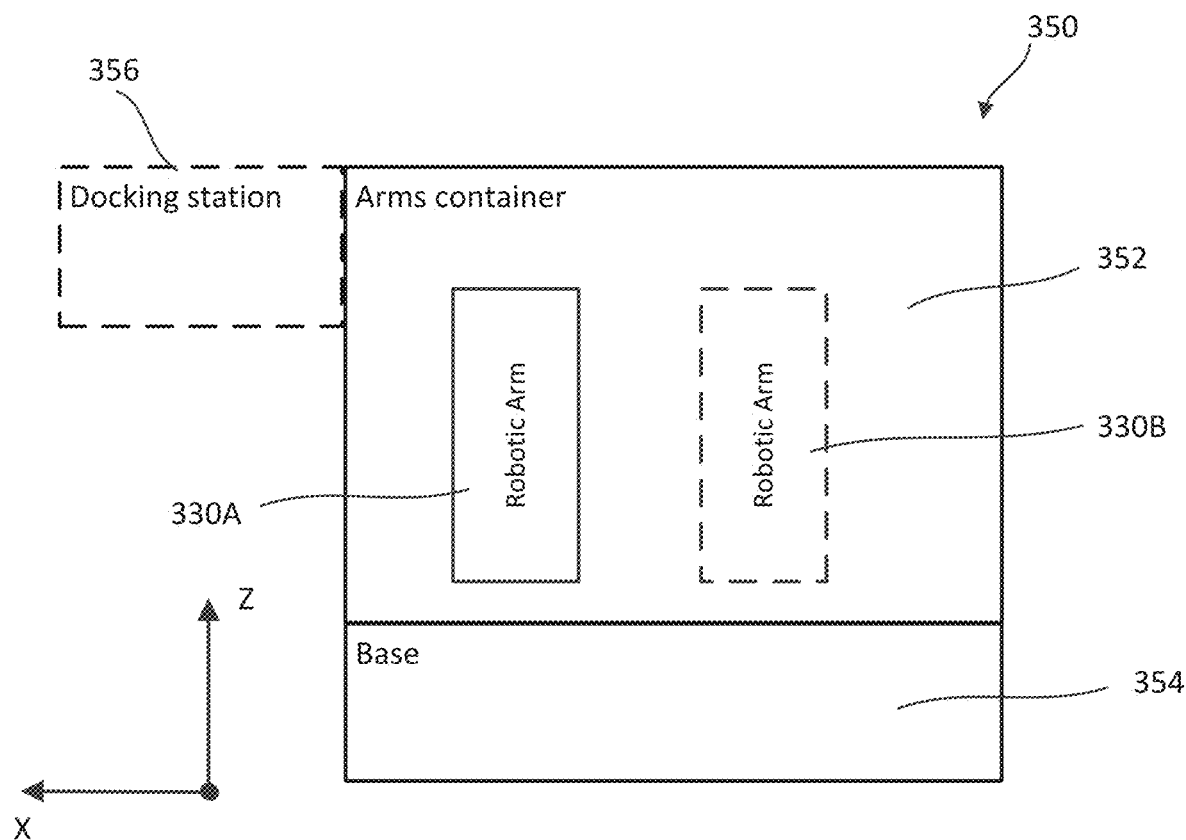
FIG. 3 is a schematic illustration of an arm cart according to an embodiment.

As shown in FIG. 3, the arm cart 350 may optionally include one or more docking stations 356 configured to be releasably attached to the surgical table and/or an arms support connected to the surgical table. In this manner, the arm cart 350 can be fixed to the surgical table and/or arms support during transfer of one or more robotic arms 330A, 330B from the arm cart 350, and then the arm cart 350 can be removed from the operating area.

The one or more robotic arms 330A, 330B can be docked and/or mounted to the surgical table using a variety of different types of coupling and/or mounting methods and mechanisms. The arm cart 350 can employ corresponding coupling methods and mechanisms to provide efficient transfer of the robotic arms 330A, 330B from the arm cart 350 to any suitable location on the surgical table and/or an arms support associated with the surgical table. In this manner, the arm cart 350 and the surgical table can include a common interface such that the robotic arms 330A, 330B can be efficiently and repeatedly coupled to and/or removed from the surgical table and the arm cart 350.

Figure 4:
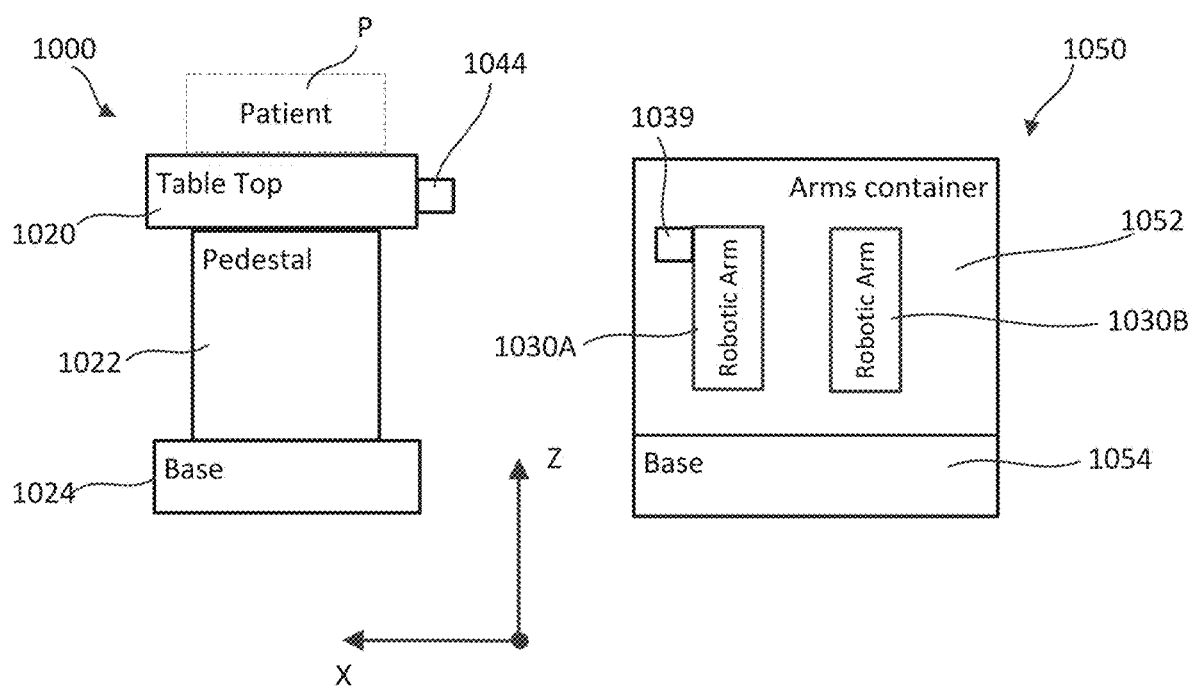
FIG. 4 is a schematic illustration of an arm cart and a surgical table, according to an embodiment.

In some embodiments, a first coupling member associated with the robotic arm can be configured to engage with a second coupling member associated with the surgical table. For example, FIG. 4 is a schematic illustration of an arm cart 1050 and a surgical table 1000. The arm cart 1050 can be the same or similar in structure and/or function to any of the arm carts described herein (e.g., arm cart 350). For example, the arm cart 1050 can include an arm container 1052 and a base 1054. The arm container 1052 is configured to support, protect, and promote sterility for one or more robotic arms (e.g., a first robotic arm 1030A and a second robotic arm 1030B) during transportation of the robotic arms, for example, from a storage area to the operating area, and during transfer of the robotic arms from the arm cart 1050 to the surgical table 1000 for use during the surgical procedure. The arm container 1052 is further configured to facilitate safe, efficient, sterile, and repeatable transfer of the surgical arms to the surgical table 1000. Transfer of the robotic arms from the arm cart 1050 to the surgical table 1000 may be performed manually. The surgical table 1000 can be the same or similar to any of the surgical tables described herein (e.g., the surgical table 100). For example, the surgical table 1000 includes a table top 1020, a support 1022, and a base 1024. A patient P can be disposed on the table top 1020.

A first coupling member 1039 is coupled to the robotic arm 1030A. A second coupling member 1044 can be coupled to the table top 1020 and/or the pedestal 1022 of the surgical table 1000. The first coupling member 1039 and the second coupling member 1044 (also referred to herein in combination as a "coupler") can include any suitable complementary releasable coupling means. In some embodiments, the arm cart 1050 and/or the surgical table 1000 can include alignment features to assist in achieving the proper alignment (e.g., along and/or about the X, Y, and/or Z axes) between the first coupling member 1039 and/or the second coupling member 1044.

Although the second coupling member 1044 is shown as being disposed to the side of the table top 1020, in some embodiments, the second coupling member can be disposed on the bottom or the top of the table top 1020. Similarly, although the second coupling member 1044 is shown and described as being coupled to the table top 1020, in some embodiments the second coupling member 1044 can be coupled to any suitable portion of the surgical table 1000, such as, for example, the pedestal 1022 or the base 1024.

Figure 5:
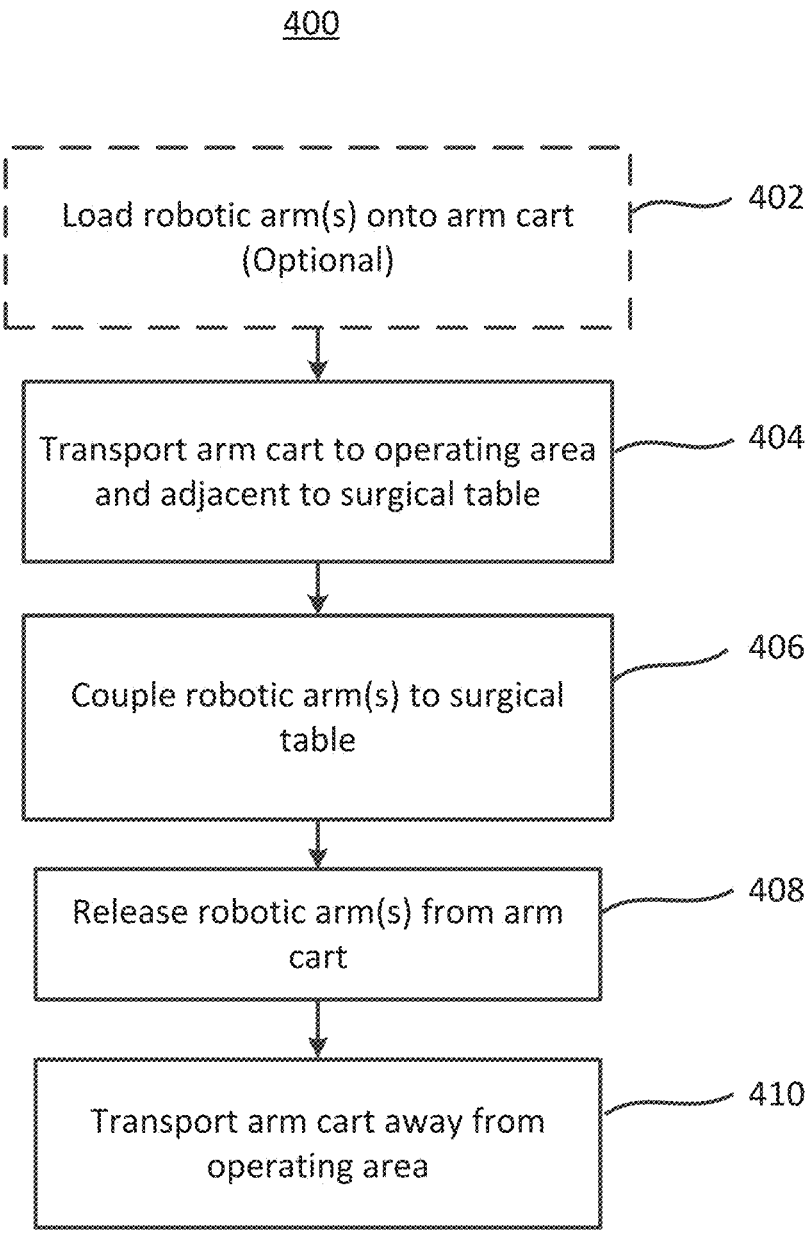
FIG. 5 is a flowchart of a method of using an arm cart to transfer robotic arms to a surgical table, according to an embodiment.

FIG. 5 is a flow chart of a method 400 of transporting and transferring surgical robotic arms to a surgical table using a surgical robotic arm cart, such as any of the arm carts described herein. The method 400 may optionally include loading one or more robotic arms onto an arm cart, at 402. For example, one or more robotic arms can be releasably coupled to an arm support of the arm cart. The arm support can be coupled to a base of the arm cart to support the one or more robotic arms above the base. In some embodiments, the arm cart may function as a storage container for the one or more robotic arms; therefore, the robotic arms may be preloaded within the arm cart and the step of loading the one or more robotic arms onto the arm cart may be omitted. The base can be freely movable on a support surface. At 404, the arm cart is transported to an operating area and adjacent to a surgical table. In some embodiments, if not yet disposed in proper alignment with the surgical table, an arm portion of a coupler disposed on at least one of the one or more robotic arms can be disposed in operative relationship with a table portion of a coupler disposed on the surgical table. At 406, the one or more robotic arms are coupled to the surgical table. For example, in some embodiments, the arm portion of the coupler can be releasably coupled to the table portion of the coupler. At 408, the one or more robotic arms are released from the arm cart. At 410, the arm cart is transported away from the operating area.

In some embodiments, if a second robotic arm has been loaded onto the arm cart (or is stored in the arm cart), the arm cart can couple a first robotic arm to the surgical table, release the first robotic arm from the arm cart, and be transported to a location adjacent to another portion of the surgical table. If not yet disposed in proper alignment with the surgical table, an arm portion of a second coupler disposed on the second robotic arm can be disposed in operative relationship with a table portion of a second coupler disposed on the surgical table. The second robotic arm can then be coupled to the surgical table via, for example, the arm portion of the second coupler being releasably coupled to the table portion of the second coupler. The second robotic arm can be released from the arm cart and the arm cart can be transported away from the operating area.

In some embodiments, an arm cart can move a robotic arm within the arm cart such that a coupling member associated with the robotic arm can be presented at a suitable location for engagement with a complementary coupling member associated with a table. For example, the arm cart can adjust the robotic arm to various height settings such that the robotic arm can cooperate with various surgical tables and/or various coupling portions of a surgical table at varying heights. In some embodiments, the arm cart can perform a first macro phase of height adjustment within the arm cart in which the robotic arm cart is set to a high, medium, or low height range. The arm cart can then be moved into position relative to the surgical table such that the coupling member of the robotic arm is aligned with a coupling member associated with the surgical table with respect to the X axis and/or Y axis. Then, in a second micro phase of height adjustment, the arm cart can move the coupling member of the robotic arm cart up or down along the Z axis into engagement with the complementary coupling member of the surgical table.

Figure 6A:
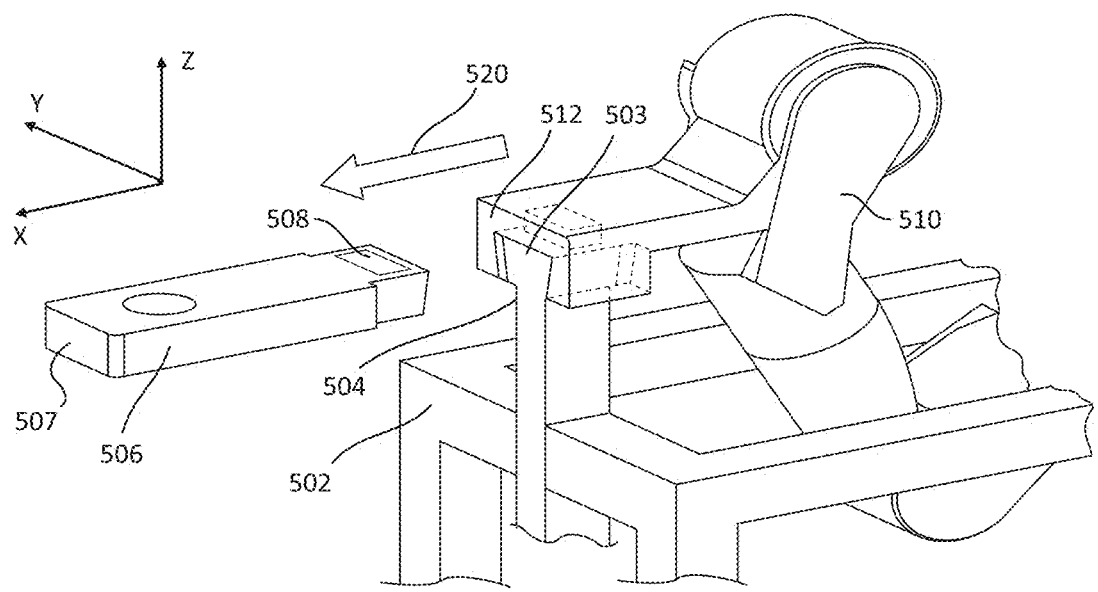
FIGS. 6A and 6B are perspective views of an arm cart capable of laterally sliding a surgical arm onto a coupling site of a surgical table, according to an embodiment.
Figure 6B:
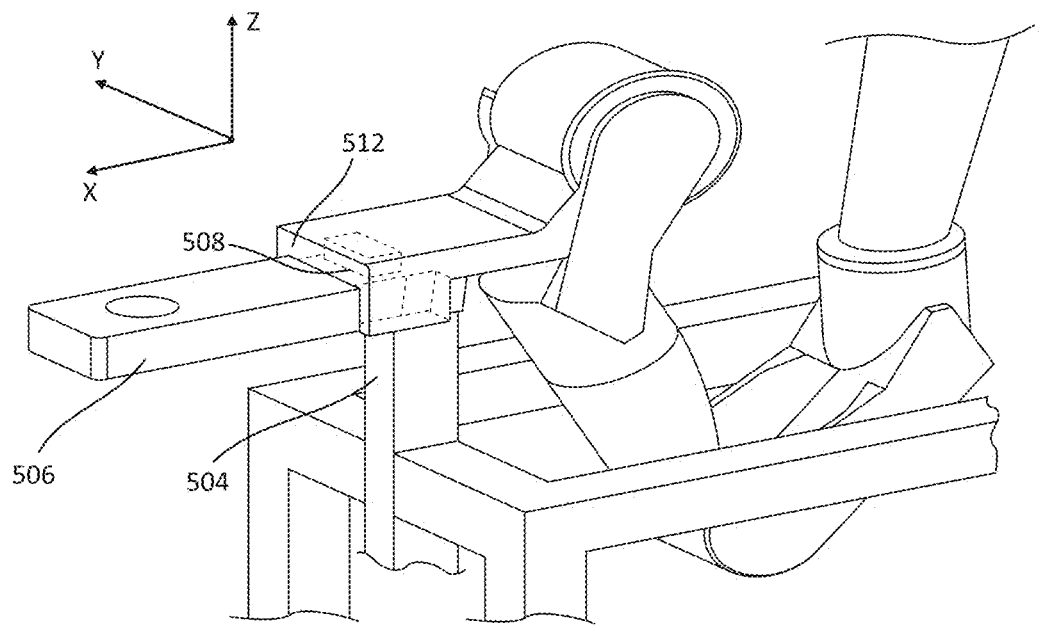

In some embodiments, a robotic arm can include a coupling member that is configured to translate along the X axis and/or Y axis to engage with a coupling member or coupling site of a surgical table. For example, a robotic arm 510 may include a coupling member 512 having a dove-tail or trapezoidal shaped opening 503, such as is shown in FIGS. 6A and 6B. The opening 503 may be designed to receive a mating dove-tail shaped portion 508 of a coupling site 506 (e.g., a table adapter drawer). The coupling site 506 can be coupled to or separate from but engageable with or coupleable to a surgical table (not depicted). For example, the coupling site 506 may have an end 507 that is coupled to a surgical table. As depicted in FIG. 6A, the robotic arm 510 may be supported in an arm cart 502. The arm cart 502 may have a support member 504 that engages with and supports a portion of the coupling member 512. The support member 504 may be lowered or raised to adjust the height of the robotic arm 510 to align the opening 503 of the coupling member 512 with the portion 508 of the coupling site 506. Alternatively or in addition to adjusting the height of the robotic arm 510, a height of the coupling site 506 may also be adjusted by, for example, adjusting a height of the surgical table.

An operator may move the arm cart 502 in a direction 520 toward the coupling site 506 to position the opening 503 of the coupling member 512 adjacent to the portion 508 of the coupling site 506. When the opening 503 of the coupling member 512 and the portion 508 of the coupling site 506 are aligned, the operator may move the robotic arm 510 such that the opening 503 slides onto and engages with the portion 508 of the coupling site 506, as shown in FIG. 6B. The mating engagement of the opening 503 with the portion 508 of the coupling site 506 creates a rigid connection between the robotic arm 510 and the surgical table. The movement of the robotic arm 510 may be restricted or controlled by the arm cart 502 such that the operator does not move the opening 503 out of alignment from the portion 508 when sliding the opening 503 onto the portion 508. For example, as depicted in FIGS. 6A and 6B, the support member 504 may also include a dove-tail shaped portion that is received in the opening 503 of the coupling member 512. Due to the mating interaction of the opening 503 and the dove-tailed shaped portion of the support member 504, the coupling member 512 of the robotic arm 510 may be limited to move in a single direction (e.g., the direction 520) toward the portion 508 of the coupling site 506. Once the opening 503 slides onto and engaged with the portion 508 of the coupling site 506, the coupling site 506 may support the robotic arm 510, and the arm cart 502 may be moved away from the robotic arm 510 and the surgical table. In some embodiments, the coupling site 506 may include additional features for attaching or locking the robotic arm 510 onto the coupling site 506. In some embodiments, the coupling site 506 may include an electrical connector that can connect to a connector disposed on the coupling member 512 to supply electrical power to the robotic arm 510 via the coupling member 512 when the coupling member 512 is engaged with the coupling site 506.

Although, in the embodiment shown in FIGS. 6A and 6B, the coupling member 512 has a dove-tail shaped opening 503 configured to slide onto and engage with a dove-tail shaped portion 508 of a coupling site 506, in other embodiments, the coupling member 512 may have a dove-tail shaped protrusion 503 that is configured to slide into and engage with a dove-tail shaped opening disposed on a coupling site. In some embodiments, the opening 503 may have a different shape (e.g., a semi-circular shape, a hexagonal shape), and the portion 508 of the coupling site 506 may be shaped correspondingly to mate with the different shape of the opening 503.

Figure 7A:
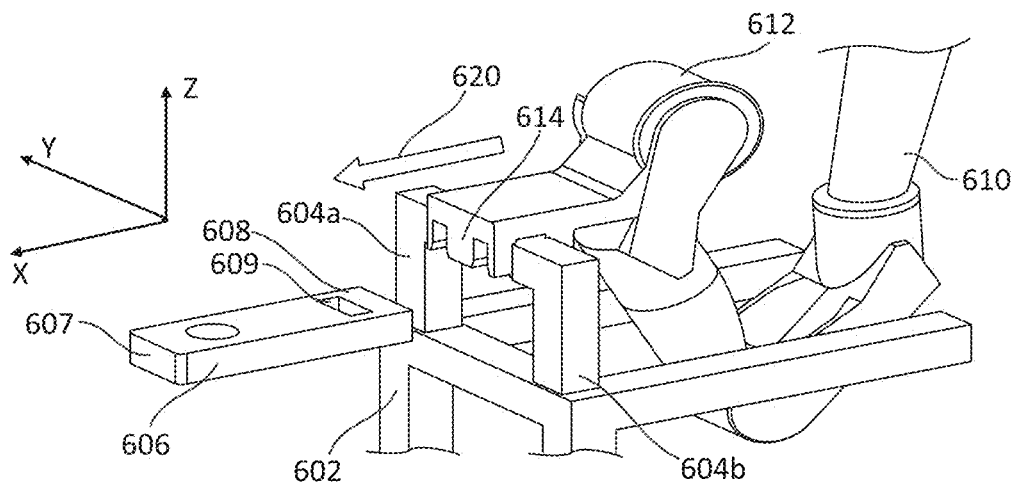
FIGS. 7A, 7B, and 7C are perspective views of an arm cart capable of lowering a surgical arm onto a coupling site of a surgical table, according to an embodiment.
Figure 7B:
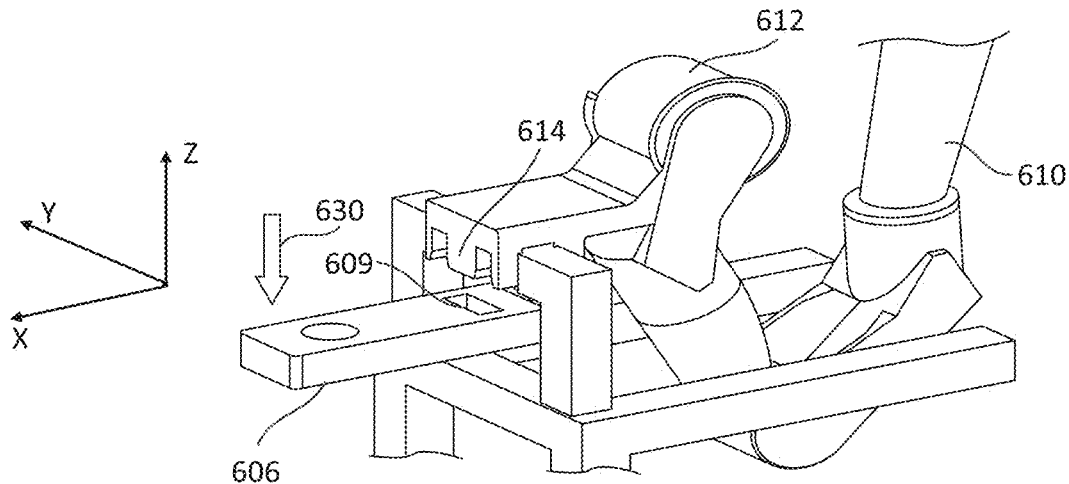
Figure 7C:
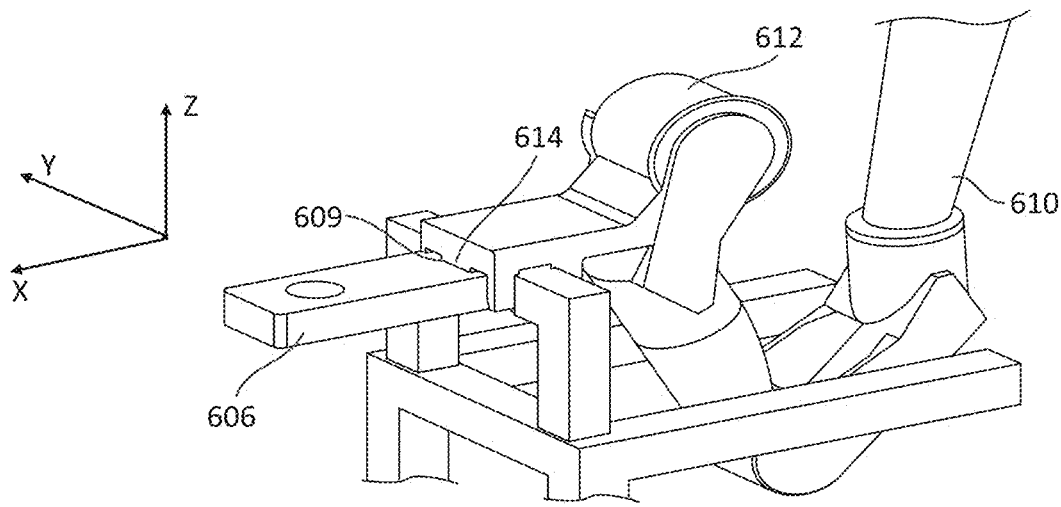

In some embodiments, a robotic arm can include a coupling member that is configured to move along the Z axis to engage with a coupling member or coupling site of a surgical table. For example, a robotic arm 610 can include a coupling member 612 having a protrusion or wedge 614, such as is depicted in FIGS. 7A-7C. The wedge 614 can be dropped down and engaged with a mating part 609 (e.g., an opening) in a coupling site 606 (e.g., a table adapter drawer). The engagement of the wedge 614 with the mating part 609 of the coupling site 606 creates a rigid mount between the robotic arm 610 and a surgical table (not depicted). The coupling site 606 can be coupled to or separate from but engageable with or couplable to the surgical table. For example, the coupling site 606 may have an end 607 that is coupled to the surgical table. The coupling site 606 may also include an electrical connector 608, which may connect to a connector (not depicted) disposed on an underside of the coupling member 612. When the electrical connector 608 connects with the connector of the coupling member 612, the surgical table can supply power to and communicate with the robotic arm 610 via the connection between the electrical connector 608 and the connector of the coupling member 612.

As depicted in FIG. 7A, the robotic arm 610 may be supported by two support members 604a, 604b of an arm cart 602. Each of the support members 604a, 604b may include a portion that fits into an opening on the underside of the coupling member 612. The support members 604a, 604b may contact or engage with the coupling member 612 at a location spaced from a location of the wedge 614 such that the wedge 614 can be lowered into the mating part 609 without being obstructed by the support members 604a, 604b. In other embodiments, a single support member or additional support members may be used to support the robotic arm 610. In other embodiments, the support members may attach to the robotic arm 610 at different locations and support the robotic arm 610 from above, below, or its sides. The support members 604a, 604b may be lowered or raised to adjust a height of the robotic arm 610, or a base or frame of the cart to which the support members 604a, 604b are attached may be lowered or raised to adjust a height of the robotic arm 610.

To attach the robotic arm 610 to the coupling site 606, the arm cart 602 may be moved in a direction 620 to a position where the wedge 614 is disposed above the mating part 609, as depicted in FIG. 7B. The support members 604a, 604b (or other portions of the arm cart 602) may be lowered to drop the wedge 614 (e.g., to move the wedge 614 downward in a direction 630) into the mating part 609, as depicted in FIG. 7C. When the wedge 614 is received in the mating part 609, the support members 604a, 604b may be removed from engagement with the coupling member 612, and the arm cart 602 may be moved away from the robotic arm 610 and the surgical table. In other embodiments, the coupling site 606 may be raised in addition to or in lieu of lowering the robotic arm 610 in order to engage the wedge 614 with the mating part 609. The coupling site 606 may be raised by adjusting a height of the surgical table, such as described above with reference to surgical table 100.

Although, in the embodiment shown in FIGS. 7A-7C, the coupling member 612 has a wedge 614 configured to engage with a mating part 609 of a coupling site 606, in other embodiments, the coupling member 612 may have an opening that can be lowered onto a mating protrusion disposed on a coupling site. In different embodiments, the wedge 614 of the coupling member 612 may also take on different shapes (e.g., a triangular shape, a trapezoidal shape), and the mating part 609 of the coupling site 606 may be shaped correspondingly to mate with the different shapes of the wedge 612.

In some embodiments, a mechanical assembly including dual locking swivel joints may be used to attach a robotic arm to a table adapter of a surgical table. The mechanical assembly may enable easy transfer of a robotic arm from the assembly to a table adapter during which the robotic arm is supported by either the assembly or the table adapter and protected from falling to the ground. The mechanical assembly may be a passive system that requires user actuation in order to transfer the robotic arm from the supporting assembly to the table adapter. During transportation and positioning of the robotic arm, the mechanical assembly may support the robotic arm. The locking swivel joints of the mechanical assembly may be configured to move an arm interface coupled to the robotic arm into alignment with the table adapter. For example, the locking swivel joints can connect one or more segments of a robotic arm support. The joints can allow the segments of the robotic arm to be to rotated about two different axes for easy positioning of the arm interface relative to the table adapter and easy transfer of the robotic arm from the arm interface to the table adapter. The assembly may also include locking mechanisms that lock the movement of the segments about the swivel joints. In their resting position, the locking mechanisms may prevent movement of the segments relative to each other, but when one or more release mechanisms are actuated (e.g., a button is depressed), the locking mechanisms may allow a user to rotate the segments about the swivel joints to place the arm into alignment with the table adapter. Once the arm is coupled to the surgical table, the arm support may be separated from the robotic arm, and the mechanical assembly (which may be mounted on a movable cart) can be moved away from the surgical table.

Figure 8:
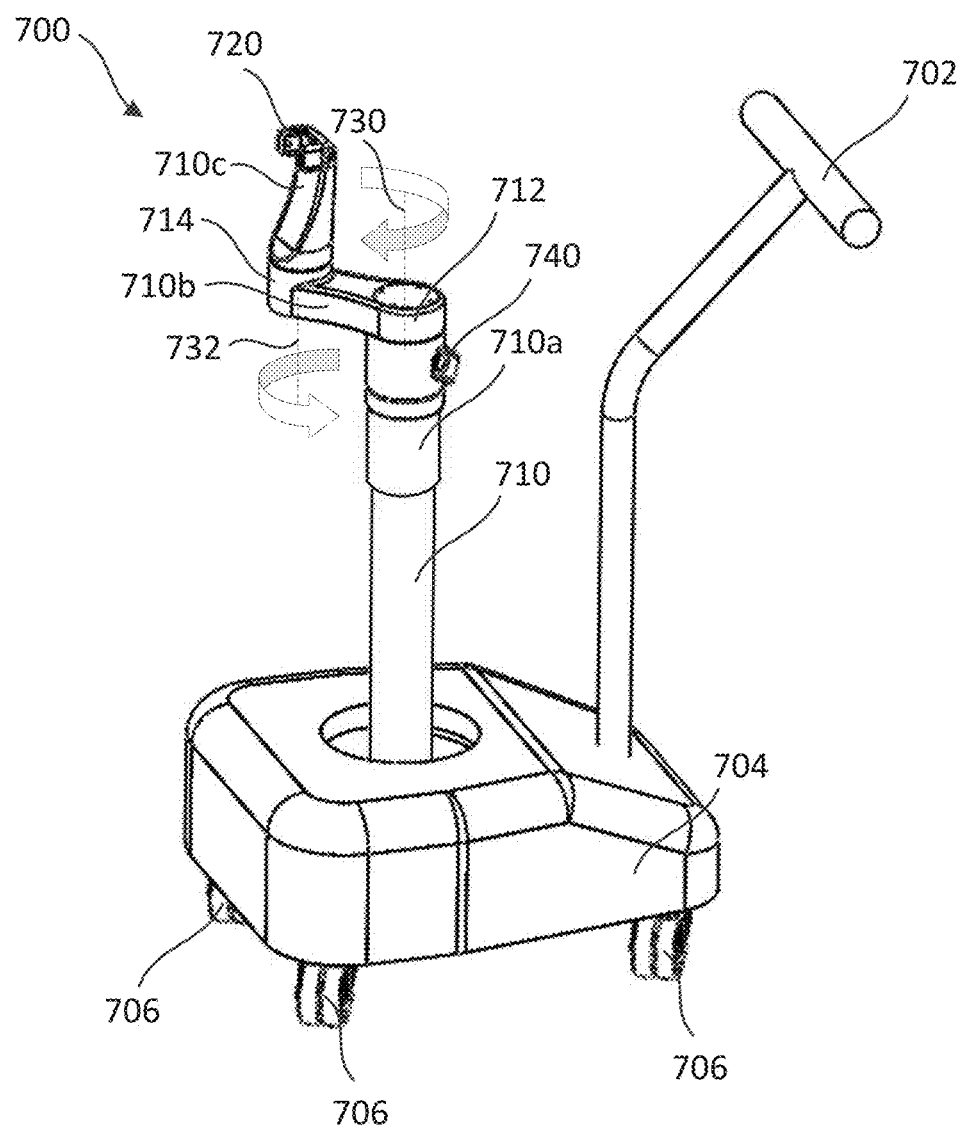
FIG. 8 is a perspective view of an arm cart having one or more swivel joints, according to an embodiment.
Figure 9A:
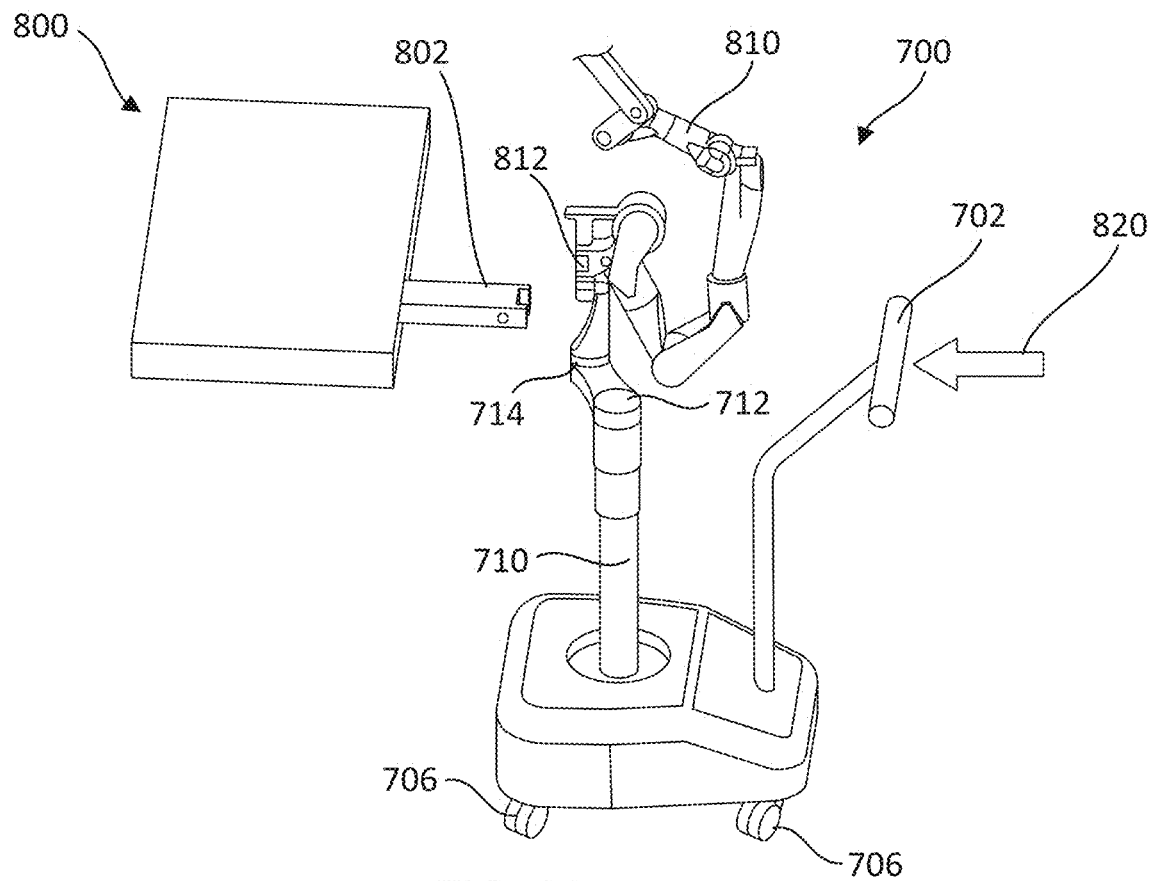
FIGS. 9A and 9B are various views of the arm cart depicted in FIG. 8 in operation, according to an embodiment.
Figure 9B:
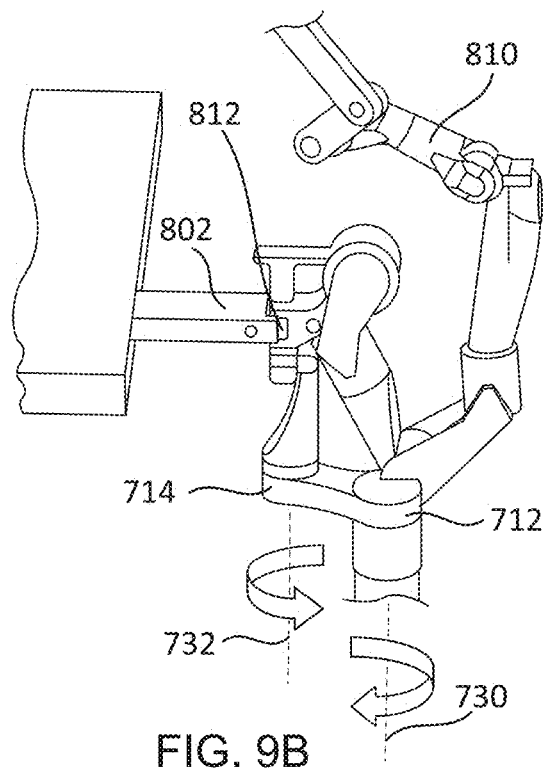

FIGS. 8, 9A, and 9B show various views of an arm cart 700 having a locking swivel system with one or more joints. FIG. 8 provides a perspective view of the arm cart 700. The arm cart 700 includes a push handle 702 and a base 704. The base 704 can be freely moveable on a support surface, such as, for example, a floor, between a first location remote from a surgical table and a second location adjacent to the surgical table. For example, as depicted in FIG. 7, the base 704 is coupled to a number of wheels 706, such as three or four wheels, such that the arm cart 700 is supported on the support surface. An operator can move the arm cart 700 along the support surface by pushing or pulling on the push handle 702. The arm cart 700 also includes an arm support 710 with a first end that is coupled to the base 704. The arm support 710 further includes a second end that can be releasably coupled to a robotic arm, such as the robotic arm 810 depicted in FIGS. 9A and 9B. As shown in FIG. 8, the arm support 710 can be coupled to a robotic arm at an attachment or support site 720. Although a single arm support 710 is depicted in FIGS. 8, 9A, and 9B, the arm cart 700 can be configured to include additional arm supports 710 that can support additional robotic arms.

As depicted in FIGS. 9A and 9B, the robotic arm 810 includes a coupling member or coupler 812. The coupler 812 can be releasably coupled to a coupling site 802 of a surgical table 800. The base 704 and the arm support 710 may control movement of the robotic arm 810. The arm support 710 includes three members or segments 710a, 710b, 710c that are coupled to each other via two joints 712, 714. Specifically, a first member 710a and a second member 710b are coupled to each other via a first joint 712, and the second member 710b and a third member 710c are coupled to each other via a second joint 714. The joints 712, 714 may be swivel joints. The arm support 710 may also include one or more locking mechanisms 740 for locking and unlocking the joints 712, 714. The locking mechanisms 740 may be fasteners (e.g., a knob or screw, a clamp) that can be loosened to unlock the joints 712, 714 to permit movement of the members 710a, 710b, 710c relative to one another. The locking mechanisms 740 may also be buttons that can be depressed to unlock the joints 712, 714 to permit movement of the members 710a, 710b, 710c. When the joints 712, 714 are unlocked, the second member 710b can rotate relative to the first member 710a about a first axis 730, and the third member 710c can rotate relative to the second member 710b about a second axis 732. The second axis 732 may be parallel to the first axis 730 or set at a slight angle to the first axis 730, depending on the angles that the members 710a, 710b, 710c are disposed relative to one another. Although each joint 712, 714 is shown to allow two members to rotate about a single axis relative to each other, the joints 712, 714 can also be configured to allow additional degrees of freedom between the members 710a, 710b, 710c. For example, each of the joints 712, 714 may be a ball-and-socket joint that allows a first member to rotate about multiple axes relative to a second member.

The joints 712, 714 are capable of moving the robotic arm 810 from a first position in which the coupler 812 of the robotic arm 810 is not engageable with the coupling site 802 of the table 800, as shown in FIG. 9A, to a second position in which the coupler 812 is engageable with the coupling site 802, as shown in FIG. 9B. The members 710a, 710b, 710c may longitudinally extend along different axes. For example, the first member 710a may extend along the first axis 730, the third member 710c may extend along the second axis 732, and the second member 710b may extend along a third axis that is orientated at a non-zero angle (e.g., 80°, 90°, 100°) relative to the first and second axes 730, 732.

Figure 10:
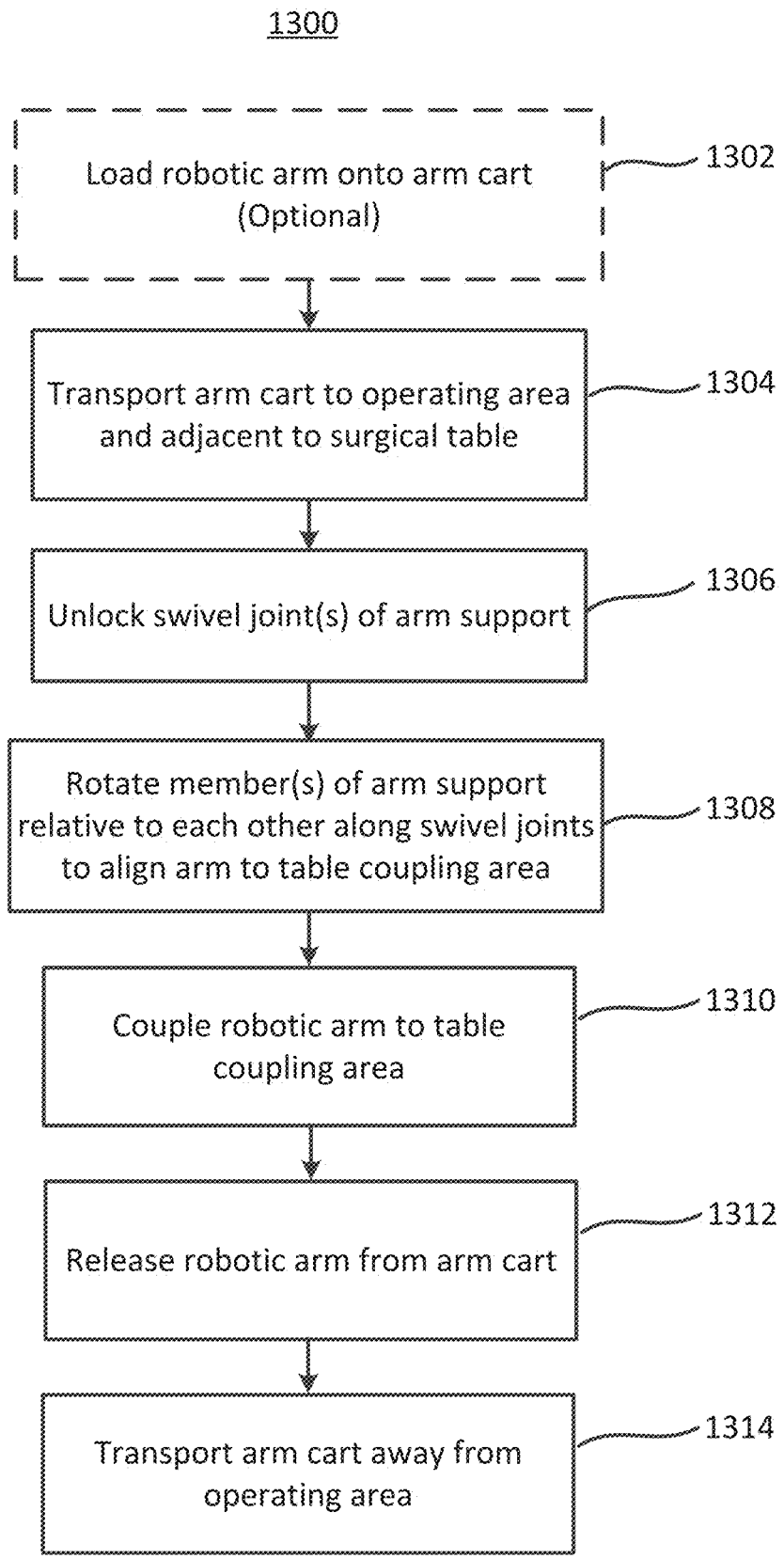
FIG. 10 is a flowchart of a method of using the arm cart depicted in FIG. 8 to transfer a robotic arm to a surgical table, according to an embodiment.

FIG. 10 is a flow chart of a method 1300 of transporting and transferring a surgical robotic arm to a surgical table using a surgical robotic arm cart, such as the arm cart 700 depicted in FIGS. 8, 9A, and 9B. At 1302, a surgical robotic arm 810 may be loaded onto the arm cart 700. For example, the robotic arm 810 may be releasably coupled to the arm support 710 of the arm cart 700. In some embodiments, the robotic arm 810 may be preloaded onto the arm cart 700 such as, for example, when the robotic arm 810 is stored prior to use in the arm cart 700; therefore, the step of loading the robotic arm 810 onto the arm cart 700 may be optional. At 1304, the arm cart 700 is moved from a first location that is remote from a surgical table, such as the surgical table 800, to a second location that is proximate to the surgical table (as generally shown by the arrow 820 in FIG. 9A). For example, the arm cart 700 may be transported to an operating area that is adjacent to the surgical table 800.

When the arm cart 700 is in the second location, the wheels 706 of the arm cart 700 can be locked to prevent the arm cart 700 from sliding out of position. The arm support 710 may also be manipulated to move the robotic arm 810 from a first position in which the coupler 812 is not engageable with the coupling site 802 of the table 800 to a second position in which the coupler 812 is engageable with the coupling site 802. Manipulating the arm support 710 may involve, for example, unlocking the first swivel joint 712 of the arm support 710 and rotating the second member 710*b* relative to the first member 710*a* about the first axis 730, and/or unlocking the second swivel joint 714 of the arm support 710 and rotating the third member 710*c* relative to the second member 710*b* about the second axis 732, at 1306 and 1308. At 1310, the robotic arm 810 may be coupled to the table 800. More specifically, the coupler 812 of the robotic arm 810 may be coupled to the coupling site 802 of the table 800. In certain embodiments, such coupling may involve sliding an opening defined by the coupler 812 onto a mating feature disposed on the coupling site 802. For example, as described above with respect to FIGS. 6A and 6B, a coupling member of a robotic arm can be coupled to a coupling site of a surgical table by sliding a dove-tail or trapezoidal shaped opening of the coupling member onto a mating structure disposed on the coupling site. At 1314, the arm cart 700 may be transported away from the table 800.

Although the arm cart 700 is described as storing, deploying, and transferring one robotic arm 810, in some embodiments the arm cart 700 can store, deploy, and transfer a second robotic arm similarly as described above with respect to the robotic arm 810. For example, both the robotic arm 810 and a second robotic arm can be loaded onto the arm cart 700 prior to transfer of either robotic arm to a surgical table. The arm cart 700 can include a second arm support and the second robotic arm can be loaded into engagement with the second arm support. After transferring the robotic arm 810 to a first coupling site of a surgical table as described above, the arm cart 700 can be moved, with the second robotic arm in a stowed configuration, via the base 704 to another location near the surgical table. The second arm support can then move the second robotic arm similarly as described above from the stowed configuration to the deployed configuration such that a coupler of the second robotic arm can be disposed in a proper position for engagement with a second coupling site associated with the surgical table. Once properly aligned with a coupling site of a surgical table, the second robotic arm can be transferred to the surgical table and the arm cart 700 can be moved away from the surgical table.

In some embodiments, a cart transfer system that has compliance in translation and rotation may be used to couple a robotic arm to a surgical table. The system may include an arm cart that can store and protect one or more robotic arms prior to coupling the arms to the surgical table. The system may also include one or more arm attachments (e.g., couplers), each of which can be attached to a robotic arm and is capable of securing the robotic arm to a table adapter. The cart transfer system allows a robotic arm to be transferred from the arm cart to the table adapter during which the arm is supported by either the arm cart or the table adapter, which minimizes the chances of the arm being dropped. The cart transfer system has compliance in translation and rotation (e.g., a portion of the system may be rotatable and translatable) to allow for correction of a misalignment between the arm cart and the table adapter. For example, a user may push the arm cart at an angle relative to the surgical table, and the system may be adjusted in translation and rotation to align an attachment area of the arm cart with the table adapter. For compliance in translation, the cart transfer system may have two linear rails that are mounted on a baseplate, and a portion of the system can be configured to translate along the two linear rails. For compliance in rotation, the cart transfer system may be configured to rotate about a vertical axis in two locations.

The arm attachment may be positioned above the table adapter and dropped on top of the table adapter. A vertical slider disposed on the arm cart may be configured to lift the arm attachment. The vertical slider can move from a first position in which it supports the arm attachment above the table adapter to a second position in which the arm attachment is lowered onto the table adapter. When the arm attachment is lowered onto the table adapter, a lever or other actuating mechanism can be moved to disengage a machined feature of the arm attachment from the arm cart and engage another machined feature of the arm attachment to the table adapter. The two machined features of the arm attachment may be a first wedge that mounts the arm attachment to the arm cart and a second wedge that mounts the arm attachment to the table adapter. The first wedge may be a female wedge, and the second wedge may be a male wedge. The two machined features can set up rigid mounts between the robotic arm and the arm cart as well as the robotic arm and the table adapter. The arm attachment may also be designed to lock the mounts into place by utilizing an over-center cam mechanism and two machined actuator linkages that can pull the wedges of the arm attachment into engagement with either the arm cart or the table adapter. When the arm attachment is locked onto the table adapter, the vertical slider can move to a third position in which it disengages from the arm attachment to allow the arm cart to be removed and pushed away from the surgical table.

Figure 11:
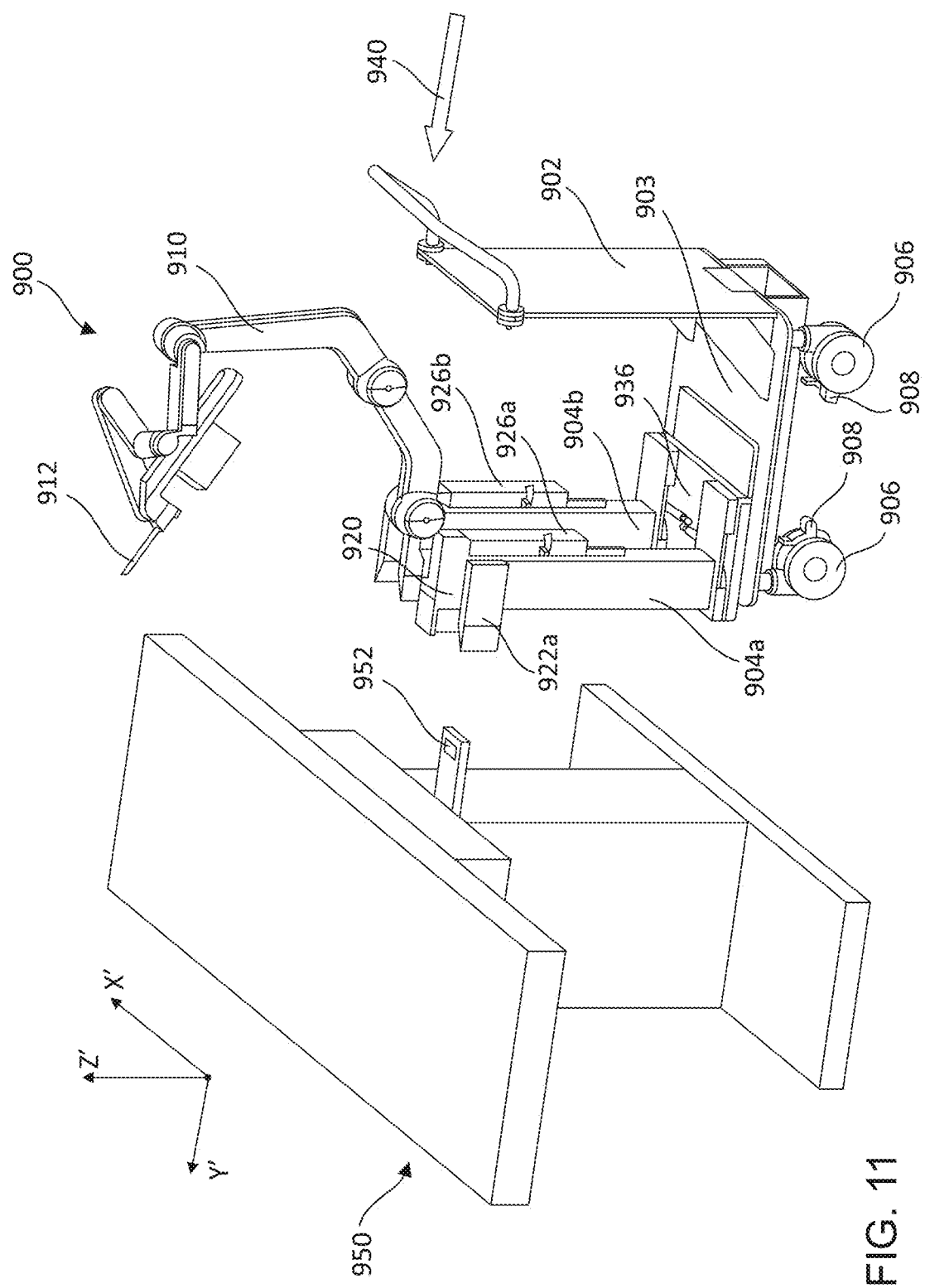
FIG. 11 is a perspective view of an arm cart having an arm support that can be rotated and translated, according to an embodiment.

FIGS. 11-16D show various views of an arm cart 900 having an arm support capable of translation and rotation, according to embodiments of the disclosure. FIG. 11 is a perspective view of the arm cart 900. As shown, the arm cart 900 has a side plate or wall 902 that is connected to a handle. The handle may be pushed by a user to move the arm cart 900 on a support surface such as, for example, a floor. The arm cart 900 also has a base 903 that is coupled to a number of wheels 906. The wheels 906 may have brakes or locks 908 that can be locked to prevent movement of the wheels 906. When the wheels 906 are unlocked, the base 903 is feely moveable on a support surface between a first location remote from a surgical table and a second location adjacent to the surgical table.

The arm cart 900 also has two arm supports 904*a*, 904*b* capable of engaging with and supporting one or more robotic arms. The two arm supports 904*a*, 904*b* are moveably coupled to a plate 936, which is attached to the base 903. As depicted in FIG. 11, a robotic arm 910 can be mounted to the first arm support 904*a*. Although not shown, in some embodiments, a second arm may also be mounted to the second arm support 904*b*. In other embodiments, the arm cart 900 may also have additional arm supports 904*a*, 904*b* that can support additional robotic arms. In some embodiments, the robotic arm 910 (and/or additional robotic arms) may be stowed or stored in the arm cart 900. In a stowed configuration, the robotic arm 910 can be disposed at least partially within the arm cart 900. During movement of the arm cart 900 on the support surface, the arm cart 900 can protect the robotic arm 910 from impact with objects. An arm attachment or coupler 920 may be disposed at a first end of the robotic arm 910. The coupler 920 can be attached to the robotic arm 910 or be separate from but engageable with or coupleable to the robotic arm 910. A second end of the arm 910 can be attached to a cannula or other surgical instrument 912.

Figure 14:
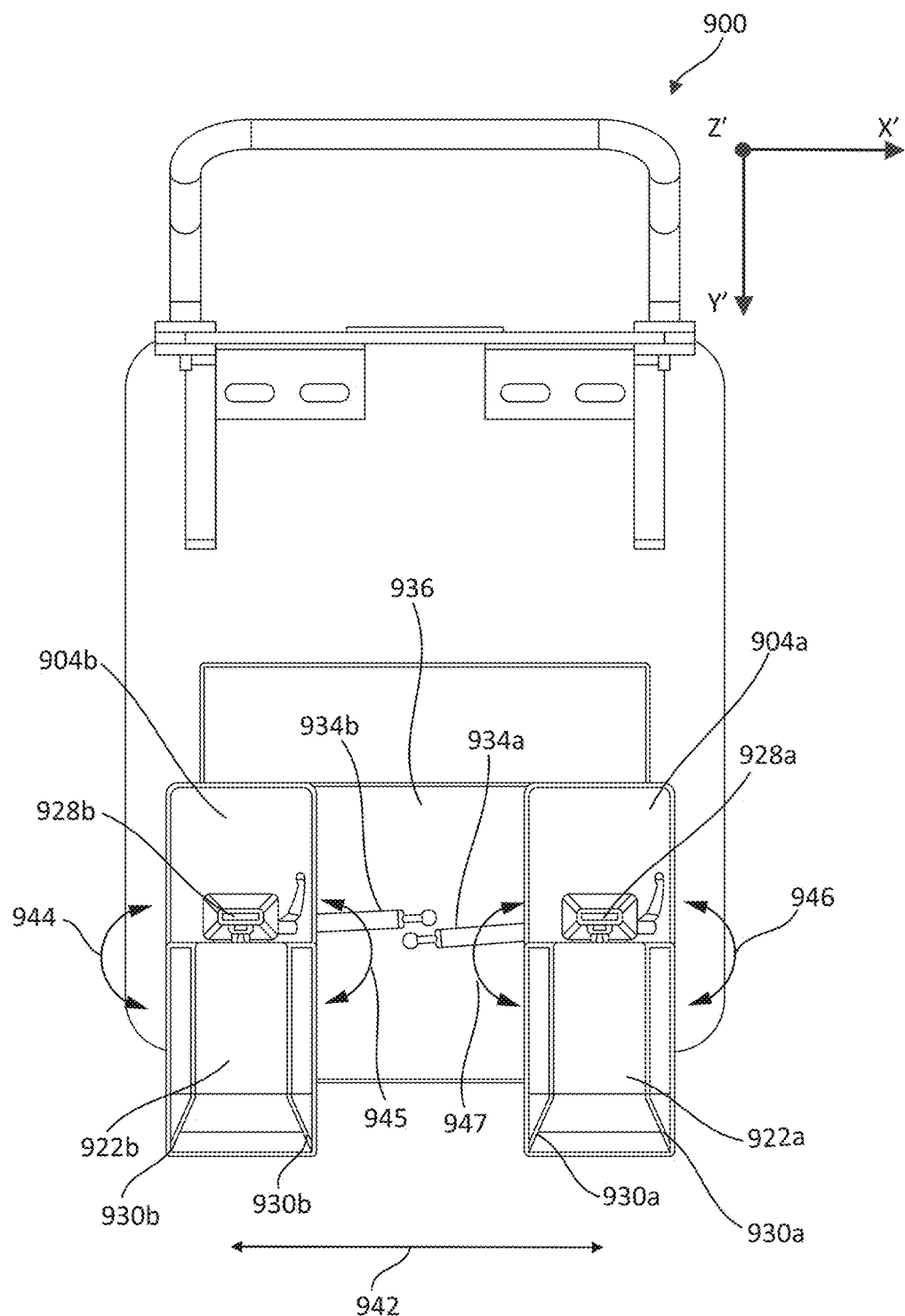
FIG. 14 is a top down view of the arm cart depicted in FIG. 11, according to an embodiment.

The arm supports 904a, 904b may be similar in construction. The first arm support 904a may have an attachment device 922a that defines an attachment area capable of receiving a table adapter or coupling site 952 of a surgical table 950. The second arm support 904b may also have a similar attachment device 922b. Referring to FIG. 14, which shows a top down view of the arm cart 900, the attachment device 922a may have one or more tapered surfaces 930a for directing the coupling site 952 into the attachment area. The attachment device 922b may also have one or more tapered surfaces 930b for directing a coupling site into its attachment area. The arm supports 904a, 904b may be moveably coupled to the plate 936. The arm support 904a may be translatable and rotatable to permit movement of the attachment area defined by the attachment device 922a such that the coupling site 952 of the table 950 can be directed into the attachment area. As shown in FIG. 14, the arm support 904a can be translated along the X' axis (along a lateral axis of the arm cart 900), as generally indicated by the arrow 942. And the arm support 904a can be rotated about the Z' axis (a vertical axis or height of the arm cart 900) in one or more locations, as generally indicated by the arrows 946, 947. The arm support 904b may also be translatable and rotatable to permit movement of the attachment area defined by the attachment device 922b (see arrows 942, 944, and 945 shown in FIG. 14). The arm cart 900 may include two linear rails 934a, 934b that are mounted on the plate 936. The arm support 904a may be mounted to the linear rail 934a such that it can translate along the linear rail 934a, and the arm support 934b may be mounted to the linear rail 934b such that it can translate along the linear rail 934b. The linear rails 934a, 934b may also be rotatable to permit the arm supports 904a, 904b to rotate.

Each arm support 904a, 904b may also have a lifting member 926a, 926b, as shown in FIGS. 11-13B. The lifting member 926a is capable of sliding up and down along a track 927a disposed on the arm support 904a, and the lifting member 926b is capable of sliding up and down a separate track disposed on the arm support 904b. The track 927a may extend vertically along the Z' axis. The lifting member 926a may support a portion of the robotic arm 910 when the lifting member 926a is in a first position, such as is shown in FIGS. 11 and 12A. In the first position, a portion of the lifting member 926a may be disposed above the attachment device 922a. For example, the lifting member 926a may have a wedge-shaped end 928a that is disposed above the attachment device 922a when the lifting member is in the first position. The wedge-shaped end 928a can be fitted into an opening 921 of the coupler 920, as best shown in FIG. 13A. The wedge-shaped end 928a of the lifting member 926a may have an opening 929a that is sized to receive a portion of an engagement member 962, further described below with reference to FIGS. 15-16D. When the wedge-shaped end 928a of the lifting member 926a is disposed in the opening 921 of the coupler 920, the lifting member 926a prevents the arm cart 900 from being separated from the robotic arm 910.

Figure 12A:
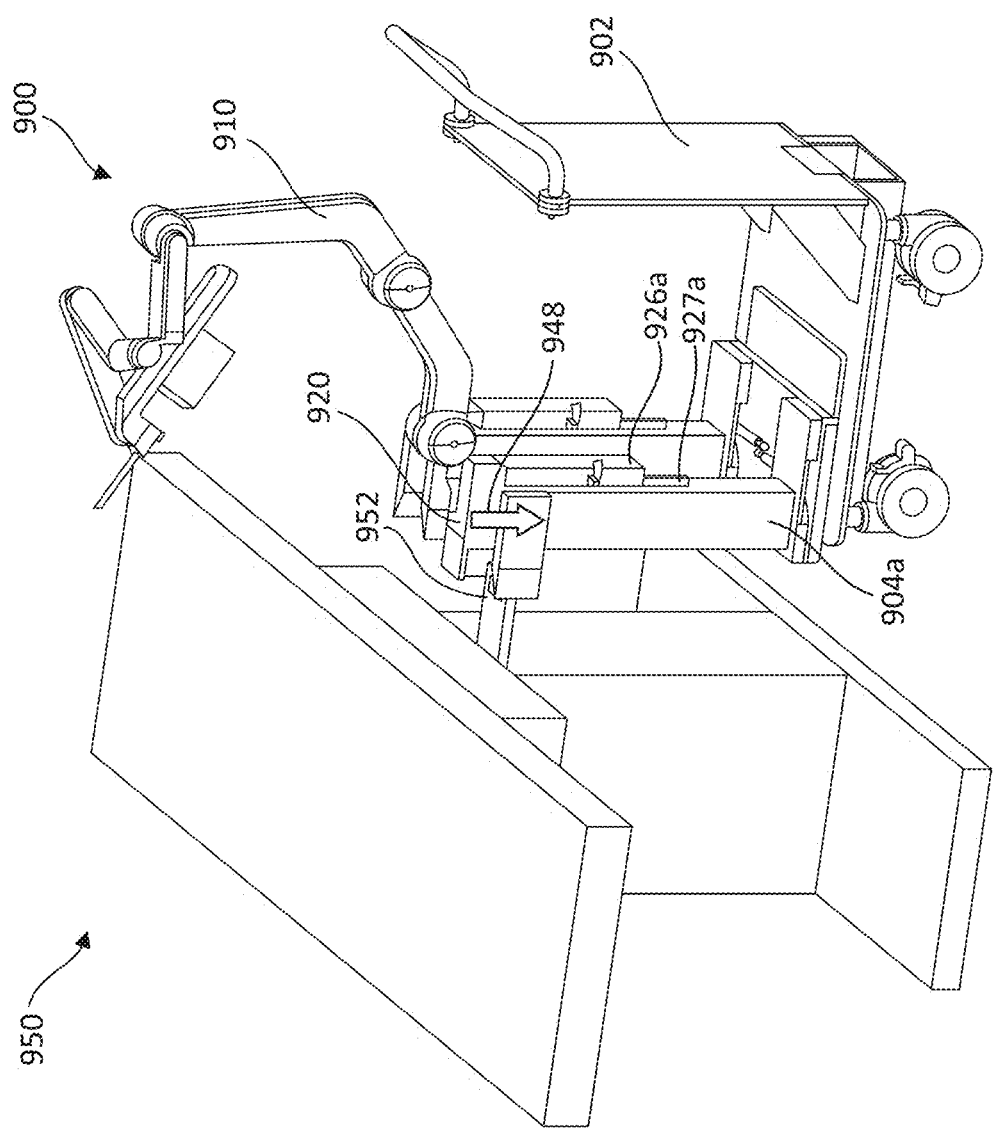
FIGS. 12A and 12B are various views of the arm cart depicted in FIG. 11 in operation, according to an embodiment.
Figure 12B:
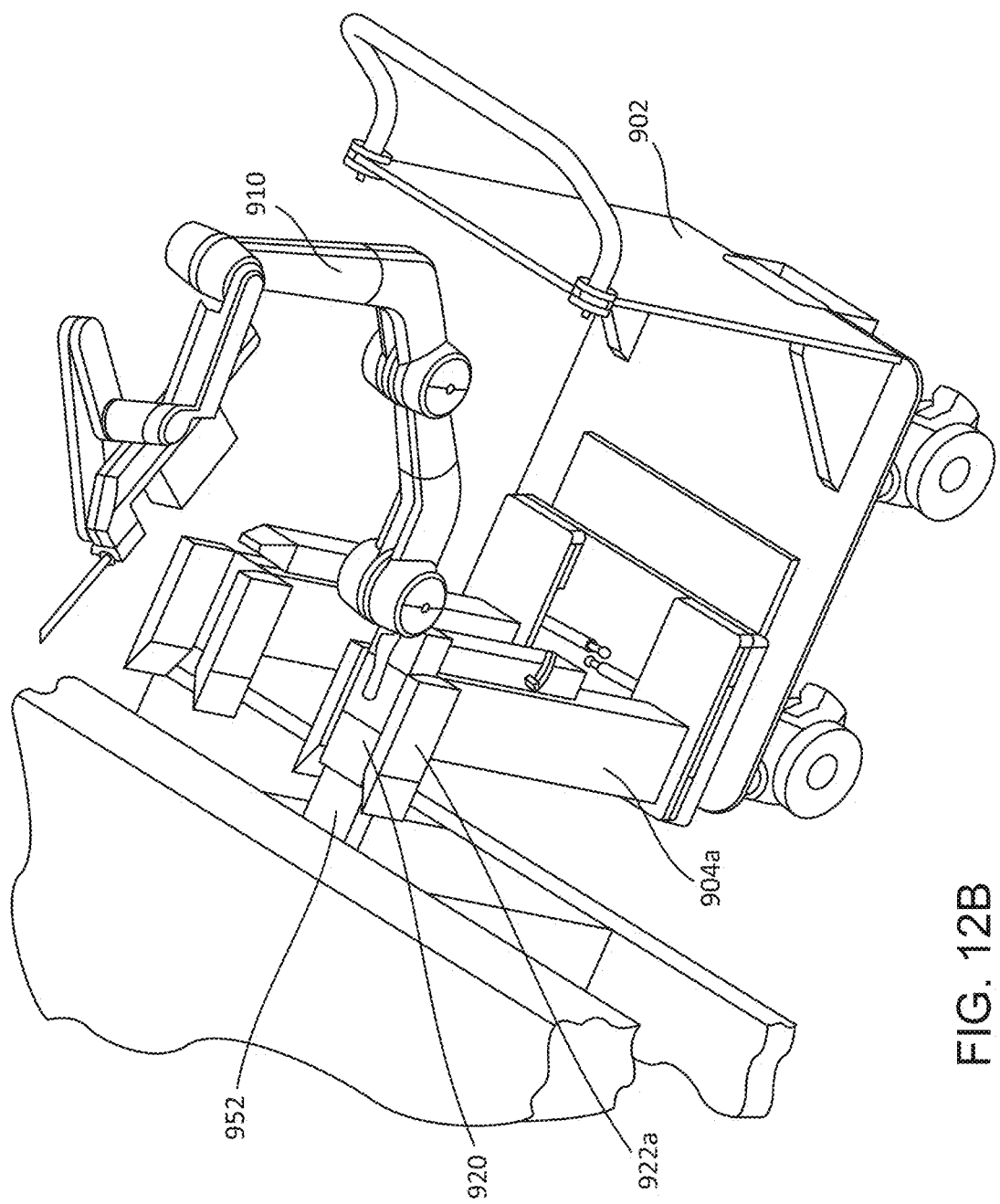
Figure 13A:
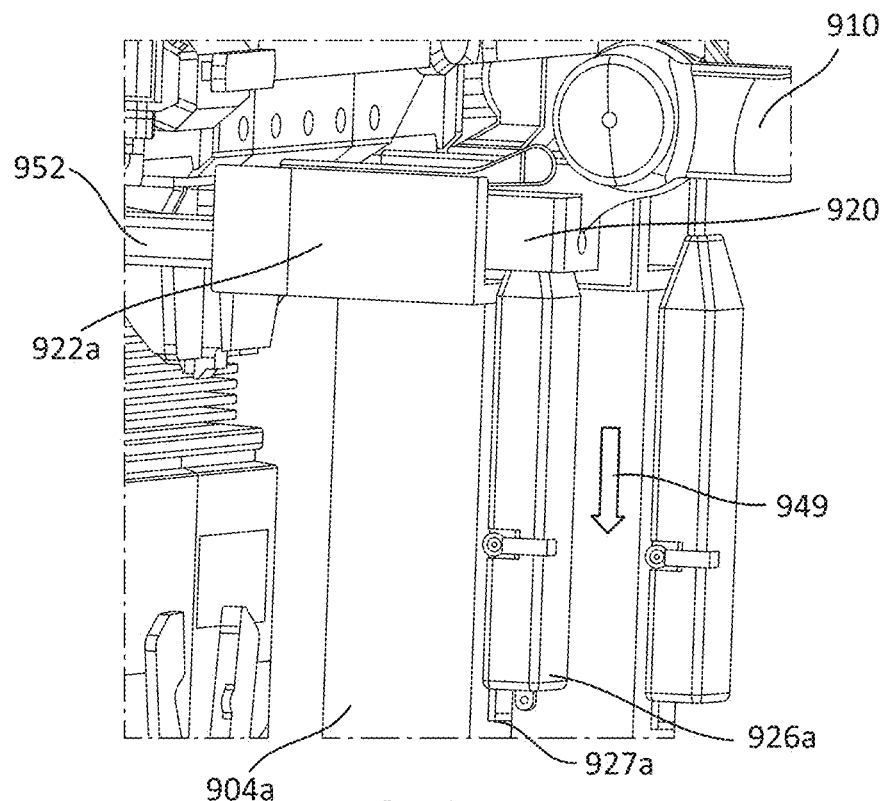
FIGS. 13A and 13B are various views of the arm cart depicted in FIG. 11 as the arm cart is decoupled from a surgical arm, according to an embodiment.
Figure 13B:
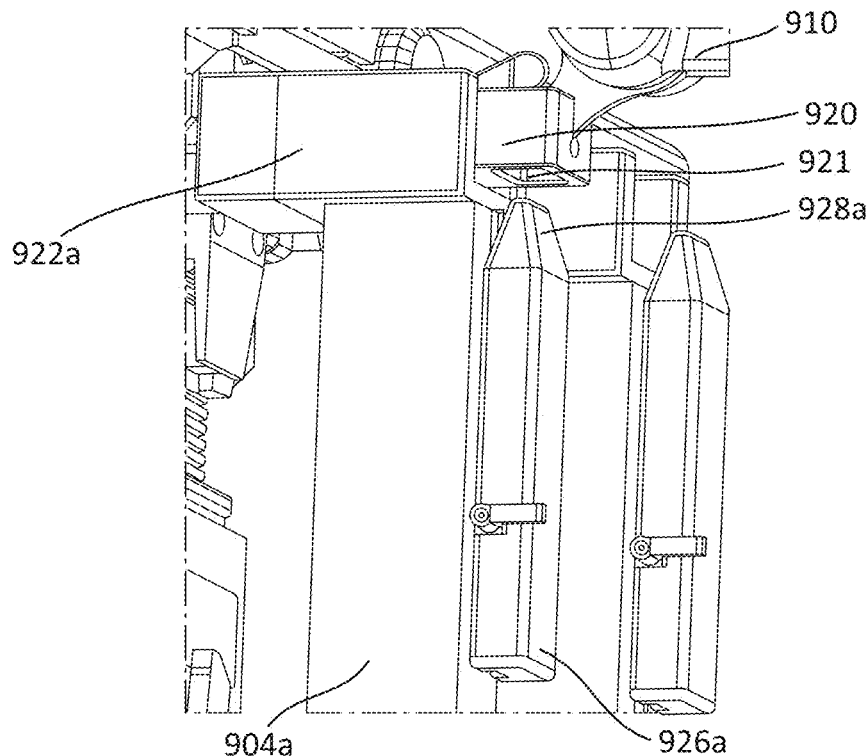

When coupling the robotic arm 910 to the coupling site 952 of the surgical table 950, the coupling site 952 may be inserted into the attachment area defined by the attachment device 922a, as shown in FIG. 12A, and the lifting member 926a may be lowered along the track 927a in a direction 920 to a second position in which the coupler 920 is dropped into place over the coupling site 952, as shown in FIG. 12B. The coupler 920 and the coupling site 952 may then be engaged with one another (using an actuator such as a lever 924, described below with reference to FIGS. 15-16D). The lifting member 926a may then be lowered along the track 927a in a direction 949 to a third position, as shown in FIG. 13B, in which the lifting member 926a is disposed below the attachment device 922a. In the third position, the lifting member 926a has been separated from the coupler 920; therefore, the arm cart 900 can be freely moved away from the surgical table 950 and the surgical arm 910 (now supported by the coupling site 952 of the surgical table 950). Although not depicted, the lifting member 926b may support a second robotic arm and function similarly as the lifting member 926b.

Figure 15:
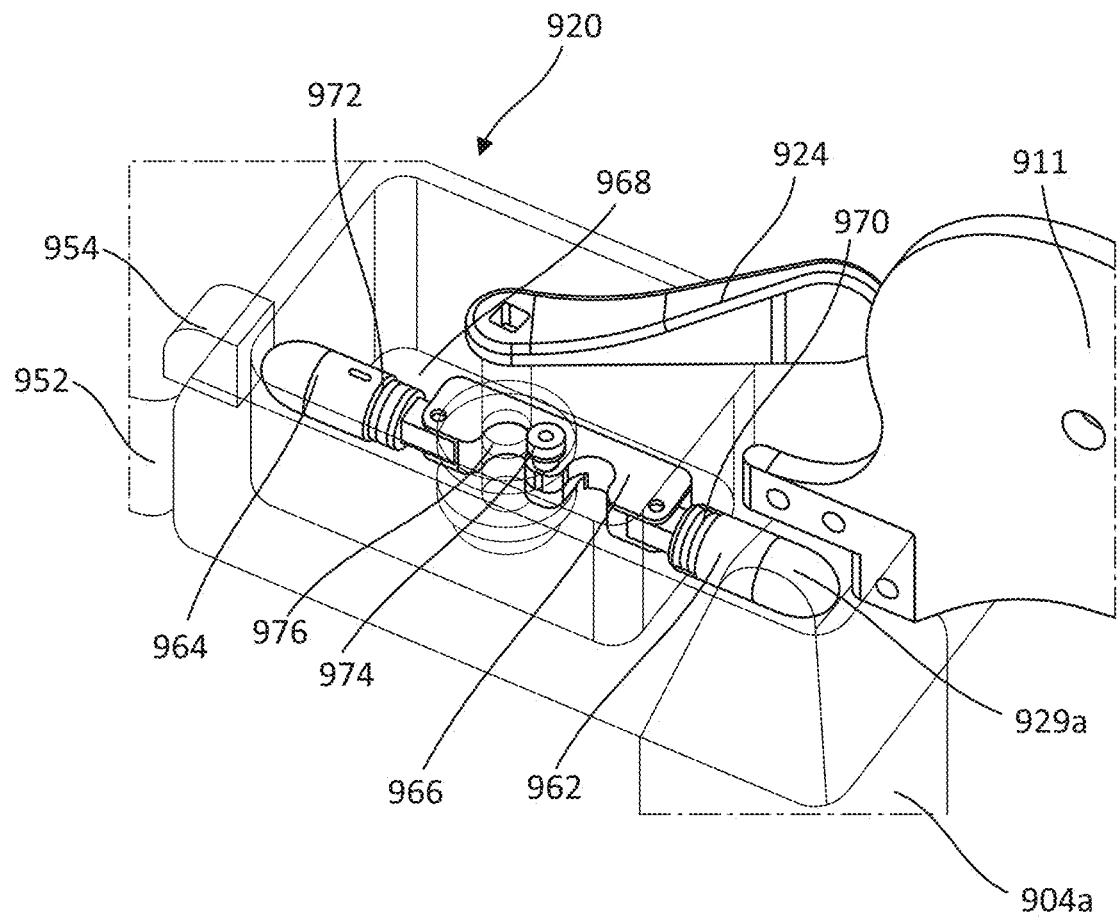
FIG. 15 is an enlarged view of an actuating mechanism of the arm cart depicted in FIG. 11, according to an embodiment.

The coupler 920 may include an actuating mechanism or actuator 924. FIG. 15 provides a detailed view of the actuator 924, and FIGS. 16A-16D show various views of the actuator 924 as it is used to disengage the coupler 920 from the arm support 904a and engage the coupler 920 to the coupling site 952 of the surgical table 950. As shown in FIG. 15, the coupler 920 is attached to a component 911 of the robotic arm 910. The coupler 920 and the component 911 may be attached to one another using conventional fasteners (e.g., bolts, nails, screws, clamps) or welding. The coupler 920 includes two engagement members 962, 964; two actuating linkages or connectors 966, 968; and two springs 970, 972. In some embodiments, the engagement members 962, 964 may be wedge pins, and the springs 970, 972 may be Belleville springs or washers, but in other embodiments, other types of engagement members (e.g., hooks, pins, screw) and springs may be used. The first engagement member 962 may be configured to releasably engage with a portion of the arm support 904a. For example, the first engagement member 962 can engage with the wedge-shaped end 928a of the lifting member 926a. The first engagement member 962 may be sized such that it can be received within the opening 929a of the wedge-shaped end 928a. When disposed within the opening 929a of the wedge-shaped end 928a, the first engagement member 962 may couple the lifting member 926a and the coupler 920 together. The second engagement member 964 may be configured to releasably engage with a portion of the coupling site 952. For example, the second engagement member 964 can be sized such that it can be received within an opening 954 of the coupling site 952. When disposed within the opening 954 of the coupling site 952, the second engagement member 964 may couple the coupling site 952 and the coupler 920 together.

Figure 16A:
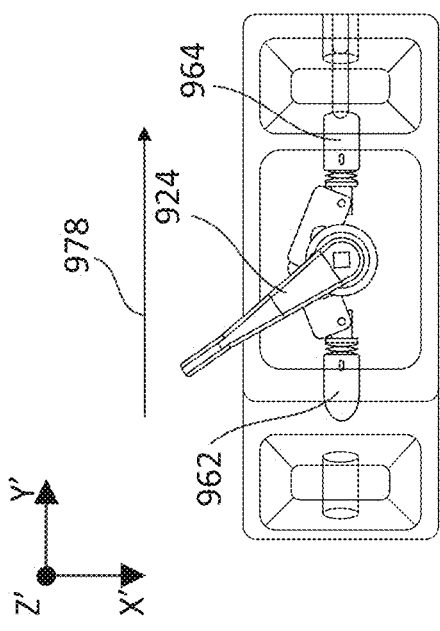
FIGS. 16A, 16B, 16C, and 16D are various views of the actuating mechanism of the arm cart depicted in FIG. 11 in operation, according to an embodiment.
Figure 16B:
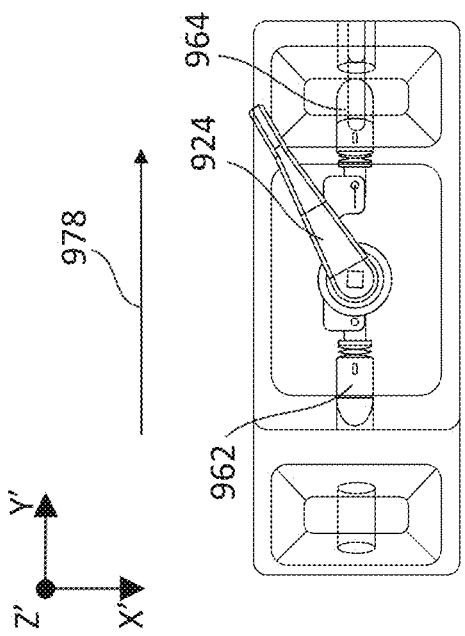
Figure 16C:
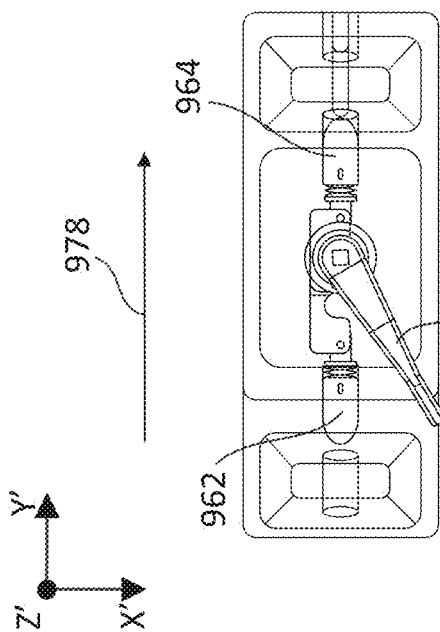
Figure 16D:
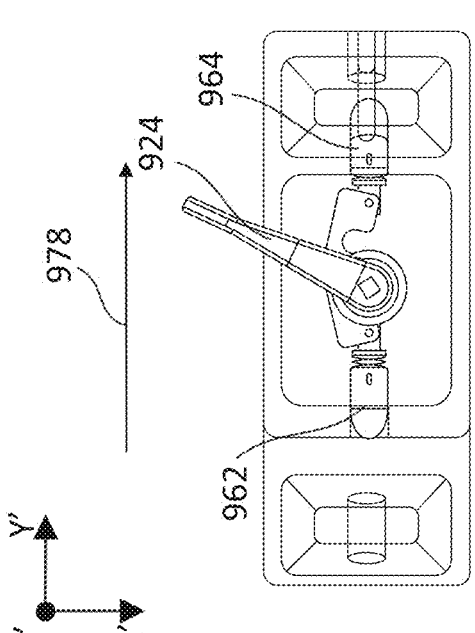

The actuator 924 may be a lever or handle, as shown in FIG. 15. The actuator 924 may be configured to engage and disengage the engagement members 962, 964 from the arm support 904a and the coupling site 952, respectively. The actuator 924 can be rotated in a clockwise direction about the Z' axis from a first position, as shown in FIG. 16A, to a second position, as shown in FIG. 16D. When rotated, the actuator 924 can drive the movement of a cam arrangement. For example, the actuator 924 can drive the movement of a rotating cam 974, which, when rotated by the movement of the actuator 924, moves the two actuating linkages 966, 968 (which function as cam followers). The actuating linkage 966 can be connected to the engagement member 962, and the actuating linkage 968 can be connected to the engagement member 964. When the actuator 924 is actuated (e.g., when the lever is rotated along the Z' axis), the engagement members 962, 964 translate in a direction 978, as shown in FIGS. 16A-16D. When the engagement members 962, 964 translate in the direction 978, the first engagement member 962 may disengage from the arm support 904a and the second engagement member 964 may engage with the coupling site 952.

In some embodiments, the actuator 924 along with the cam 974, the actuating linkages 966, 968, and the springs 970, 972 may function as an over-center locking mechanism. For example, the actuator 924 can be rotated beyond a center position in which the two actuating linkages 966, 968 are disposed horizontally or aligned along the Y' axis (a longitudinal axis of the arm cart 900) to an over-center position. In the over-center position, the actuator 924 may be biased away from the center position, thereby locking the various components in place and preventing any unintentional disengagement of the coupler 920 from the arm support 904*a* or the coupling site 952. For example, when engaging the second engagement member with the coupling site 952, the actuator 924 may be rotated in the clockwise direction until the two actuating linkages 966, 968 are disposed horizontally (as shown in FIG. 16D) and then rotated further such that the two actuating linkages 966, 968 move past their center position to an over-center position. In the over-center position, a user must overcome a spring force in order to move back to the center position; therefore, the actuator 924 is biased away from the center position by the spring force. Having an over-center arrangement may prevent accidental movement of the actuator 924, thereby minimizing the risk of the robotic arm 910 from being decoupled or disengaged from the arm cart 900 or the surgical table 950.

Figure 17:
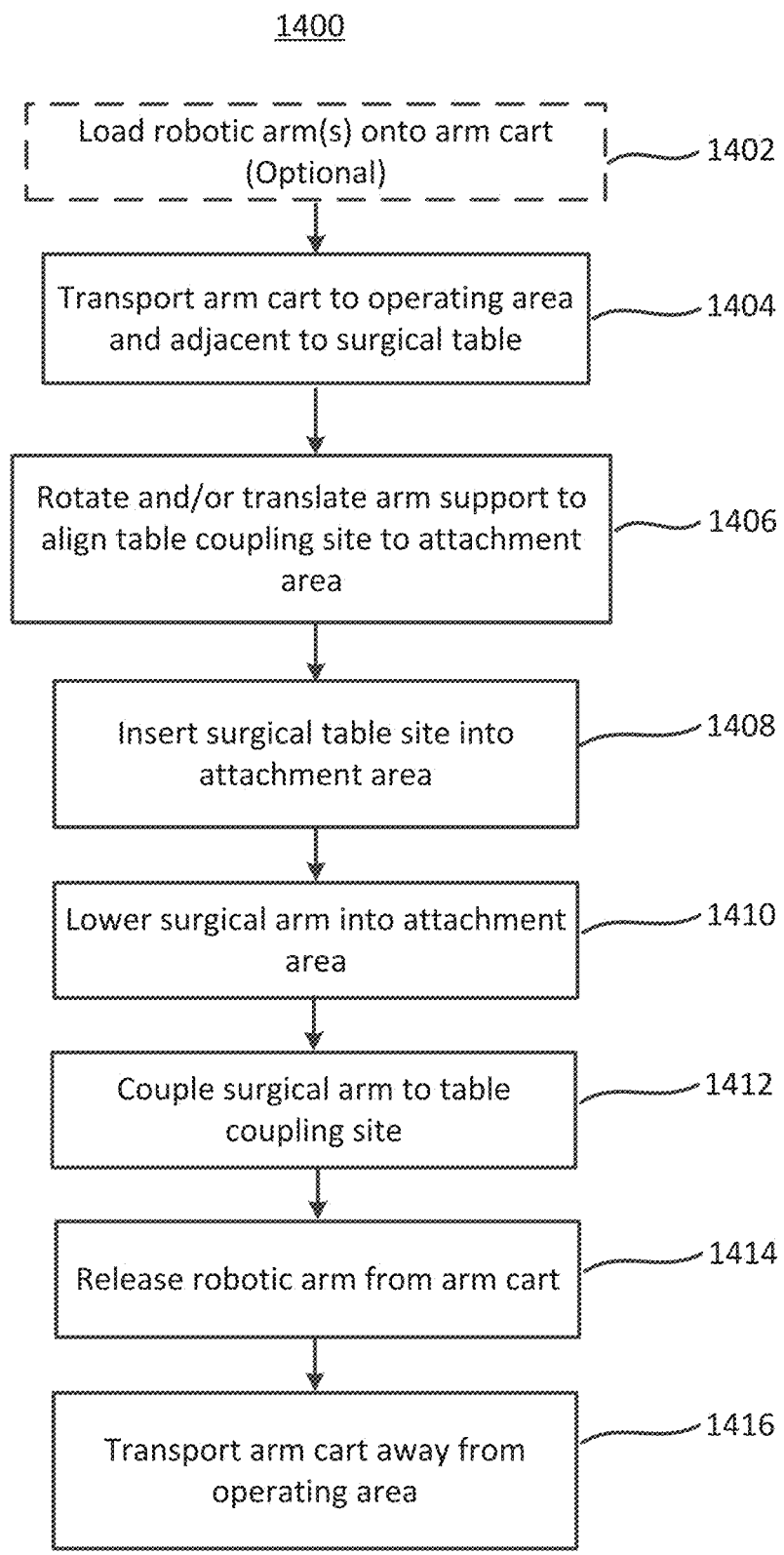
FIG. 17 is a flowchart of a method of using the arm cart depicted in FIG. 11 to transfer a robotic arm to a surgical table, according to an embodiment.

FIG. 17 depicts a flow chart of a method 1400 of transporting and transferring a surgical robotic arm to a surgical table using a surgical robotic arm cart, such as the arm cart 900 depicted in FIGS. 11-16D. At 1402, a surgical robotic arm 910 may be loaded onto the arm cart 900. For example, the surgical robotic arm 910 can be attached to a coupler 920, which can be coupled to the arm support 904*a* of the arm cart 900. In some embodiments, this step of loading the robotic arm 910 onto the arm cart 900 may be optional as the arm cart 900 may function as a storage container for the robotic arm 910 and, therefore, the robotic arm 910 may already be pre-loaded onto the arm cart 900. At 1404, the arm cart 900 is moved from a first location that is remote from a surgical table, such as the surgical table 950, to a second location that is proximate to the surgical table (as generally shown by the arrow 940 in FIG. 11). For example, the arm cart 900 may be transported to an operating area that is adjacent to the surgical table 950. As described above, the arm cart 900 can include a plurality of wheels 906, which allow the arm cart 900 to be freely moved along a support surface such as a floor.

When the arm cart 900 is at the second location, the wheels 906 of the arm cart 900 can be locked to prevent the arm cart 900 from moving when the robotic arm 910 is being transferred from the cart 900 to the surgical table 950. At 1406, the arm support 904*a* is translated or rotated in order to align the attachment area defined by the attachment device 922*a* with the coupling site 952 of the surgical table 950. When the attachment area and the coupling site 952 are aligned, the coupling site 952 can be inserted into the attachment area, at 1408, as shown in FIG. 12A. The tapered surfaces 930*a* may help guide the coupling site 952 into the attachment area. At 1410, the robotic arm 910 may be lowered into the attachment area such that the coupler 920 is placed over the coupling site 952, as shown in FIG. 12B. The robotic arm 910 can be lowered into the attachment area by moving the lifting member 926*a* downwards along the Z' axis from a first position in which the wedge-shaped end 928*a* of the lifting member 926*a* is disposed higher than the attachment device 922*a*, as shown in FIG. 12A, to a second position in which the wedge-shaped end 928*a* is positioned at substantially the same height as the attachment device 922*a*, as shown in FIG. 12B.

At 1412 and 1414, the robotic arm 910 via the coupler 920 is disengaged from a portion of the arm support 904*a* and engaged with a portion of the coupling site 952. In some embodiments, the coupler 920 has a first engagement member 962 and a second engagement member 964 that are configured to engage with the portion of the arm support 904*a* and the portion of the coupling site 952, respectively. The two engagement members 962, 964 may be disengaged and engaged with the arm support 904*a* and the coupling site 952 by moving the actuator 924. The actuator 924 may be, for example, a lever which is moveable between a first position, as shown in FIG. 16A, and a second position, as shown in FIG. 16D. When the lever is rotated clockwise through the positions shown in FIG. 16A-16D, the first engagement member 962 disengages from the portion of the arm support 904*a* (e.g., the wedge-shaped end 928*a* of the lifting member 926*a*) and the second engagement member 964 engages to the coupling site 952. In some embodiments, the robotic arm 910 may be attached to a different coupler that is capable of coupling to a coupling site of a surgical table, such as, for example, the coupling member 612 described above with reference to FIGS. 7A-7C.

To release the robotic arm 910 from the arm cart 900, the lifting member 926*a* may be lowered to a third position in which the lifting member 926*a* is separated from the robotic arm 910 (e.g., the wedge-shaped end 928*a* of the lifting member 926*a* is no longer disposed in the opening 921 of the coupler 920), at 1414. At 1416, the arm cart 900 can be freely moved away from the robotic arm 910 and the surgical table 950.

In some embodiments, a mechanical assembly having an actuating mechanism, such as, for example, a pivoting lever, can be used to lift and lower a robotic arm onto a table adapter for attachment to the table adapter. The mechanical assembly may be mounted on an arm cart, which can be used to store one or more robotic arms prior to coupling the arms to a surgical table. The mechanical assembly may enable easy transfer of a robotic arm from the arm cart to a table adapter during which the robotic arm is supported by either the arm cart or the table adapter and, thus, protected from falling to the ground. The mechanical assembly includes an actuating mechanism such as a pivoting lever. The pivoting lever may function like a see-saw, e.g., the pivoting lever may be designed to pivot about a pivot point. A user can operate the lever by pressing down on a first end of the lever in order to raise or lift a second end of the lever. The second end of the lever may be coupled to an arm support, which is releasably coupled to the robotic arm. Accordingly, when the user presses down on the first end of the lever, the second end of the lever lifts the robotic arm.

The robotic arm may have an arm interface or coupler that can couple to a table adapter. When the robotic arm is stored on the arm cart, the arm interface may be coupled to an attachment interface disposed on the arm cart. When the robotic arm is lifted, the arm interface may separate from the attachment interface disposed on the arm cart. The arm interface may then be positioned above the table adaptor, and the user may release the first end of the lever to lower the arm interface onto the table adapter. The table adapter may have a second attachment interface to which the arm interface can couple. This arrangement may allow a user to remain on one side of the arm cart (e.g., behind the arm cart) when transporting and transferring a robotic arm from the arm cart to the surgical table. For example, this arrangement would not require a user to move from behind the arm cart to a front side or lateral side of the arm cart in order to align certain components of the arm cart with the table adapter. The arrangement also allows the arm cart and the table adapter to have identical attachment interfaces, which may be useful if the arm needs to be supplied with power when it is coupled to the arm cart.

FIGS. 18-21 show side views of an arm cart 1100 with an actuating mechanism 1132 in four configurations during a coupling operation. The actuating mechanism 1132 may be configured to lift and lower a robotic arm 1110. The robotic arm 1110 may have a coupler 1112 (e.g., an arm attachment) that can be releasably coupled to a coupling site 1152 of a surgical table 1150. The arm cart 1100 may have a base 1104 to which a plurality of wheels 1106 may be mounted. The plurality of wheels 1106 may allow the arm cart 1100 to be freely moveable on a support surface, such as, for example, a floor, between a first location remote from a surgical table and a second location adjacent to the surgical table. The arm cart 1100 may be configured to support, protect, and promote sterility for a robotic arm 1110 during transportation of the robotic arm 1110, for example, from a storage area to an operating area, and during transfer of the robotic arm 1110 from the arm cart 1100 to the surgical table 1050 for use during a surgical procedure.

The actuating mechanism 1132 may be a lever that can rotate about a pivot point 1120. The actuating mechanism 1132 may include a first segment 1134 and a second segment 1136, which connect at the pivot point 1120. The first segment 1134 may be angled with respect to the second segment 1136 such that the two segments 1134, 1136 form a bend in the actuating mechanism 1132 at the pivot point 1120. The actuating mechanism 1132 may be actuated through any suitable actuation means. For example, the actuating mechanism 1132 can be user-actuated. As shown in FIGS. 18-21, a user 1130 may stand on a first side of the cart 1100 and push down on the first segment 1134 to actuate the actuating mechanism 1132. The actuating mechanism 1132 can be used to lift the coupler 1112 of the robotic arm 1110 and lower the coupler 1112 into engagement with, for example, a coupling site 1152 associated with the surgical table 1150.

Figure 18:
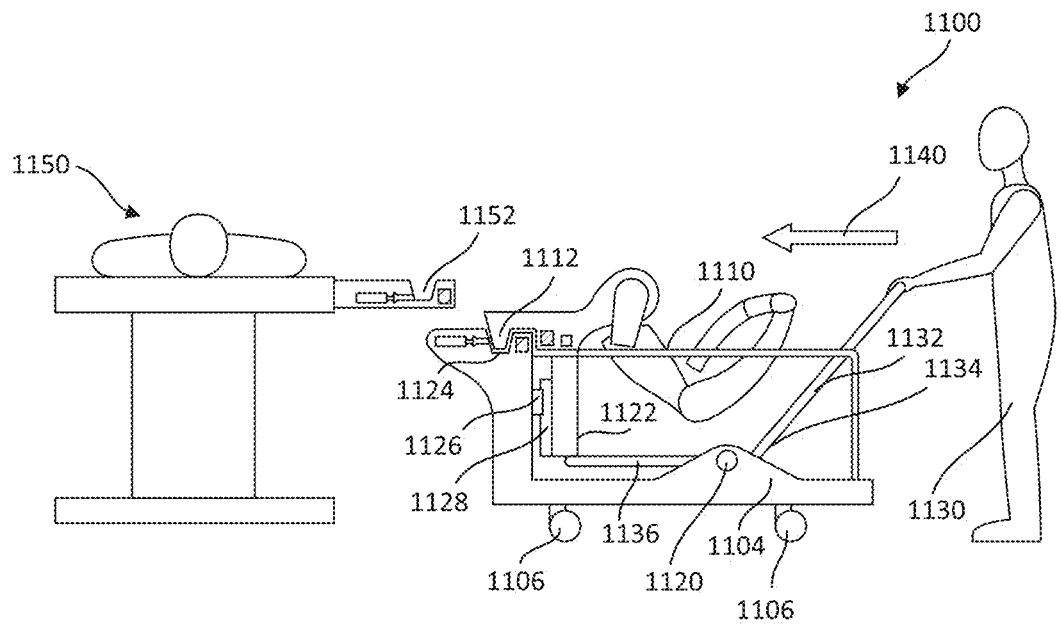
FIGS. 18, 19, 20, and 21 are illustrations of an arm cart capable of lifting a surgical arm using a mechanical pivoting member, according to an embodiment.

As depicted in FIG. 18, the arm cart 1100 can support the robotic arm 1110 in a first, stowed position. In the stowed position, the coupler 1112 of the robotic arm 1110 may be coupled to an attachment site 1124 disposed on the arm cart 1100. In some embodiments, the attachment site 1124 may include an electrical connector that is capable of connecting with an electrical connector disposed on the coupler 1112 and provide power and/or communicate with the robotic arm 1110. In the stowed position, the robotic arm 1110 may also be releasably coupled to a first end of an arm support 1122. The arm support 1122 can include a guide member 1128 that defines a linear track. The arm cart 1100 can include a follower 1126 that is disposed in the linear track and configured to translate along the linear track. The follower 1126 can be mounted on a side portion of the arm cart 1100. In other embodiments, the follower 1126 can be mounted on the arm support 1122, and the guide member 1128 can be mounted on a side portion of the arm cart 1100.

Figure 19:
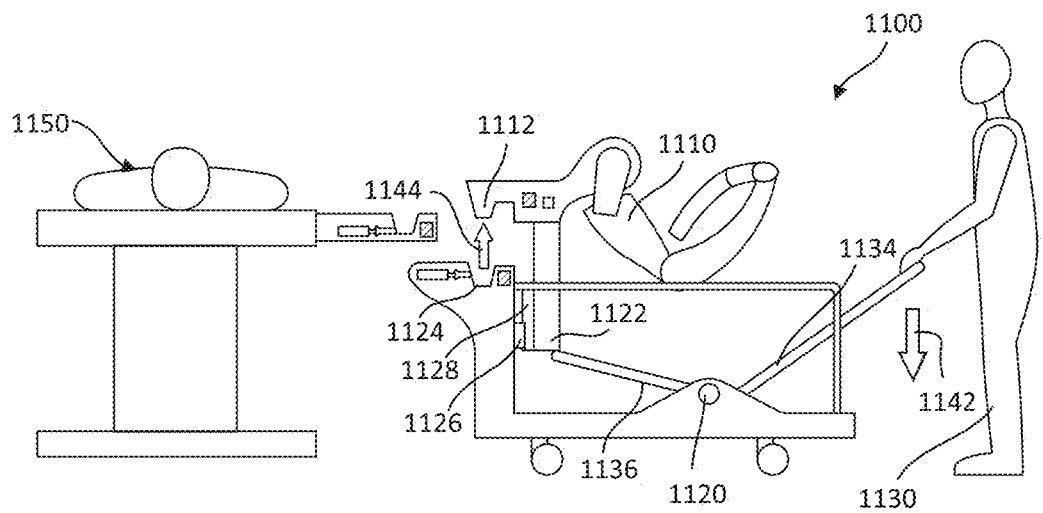
Figure 21:
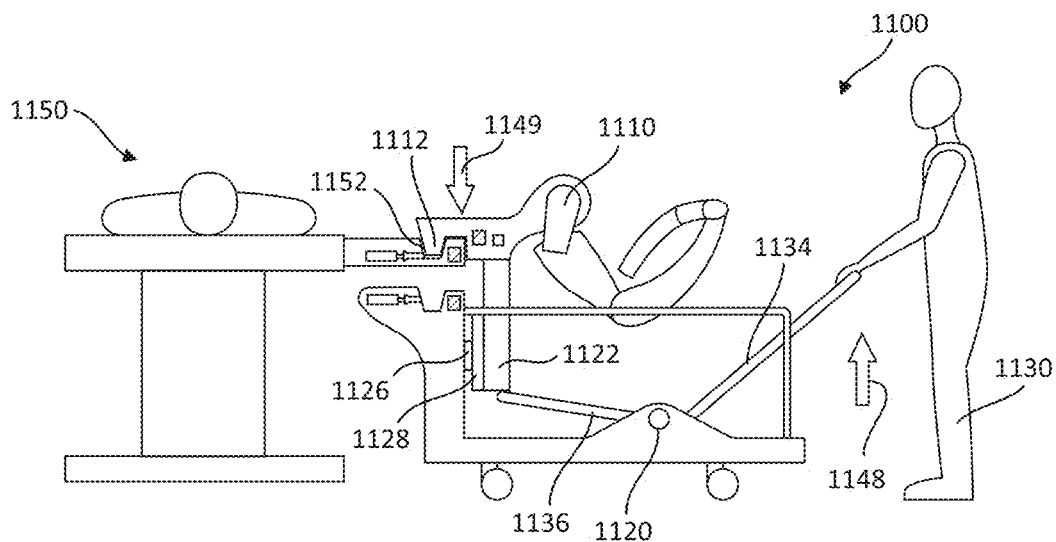

The actuating mechanism 1132 may engage with a second end (opposite to the first end) of the arm support 1122. In operation, the actuating mechanism 1132 may be configured to move the arm support 1122 from a first position, as depicted in FIG. 18, to a second position, as depicted in FIG. 19, and further to a third position, as depicted in FIG. 21. When the arm support 1122 moves from the first position to the second position, the follower 1126 may translate in a first direction along the linear track, and when the arm support 1122 moves from the second position to the third position, the follower 1126 may translate in a second direction opposite to the first direction along the linear track.

Figure 20:
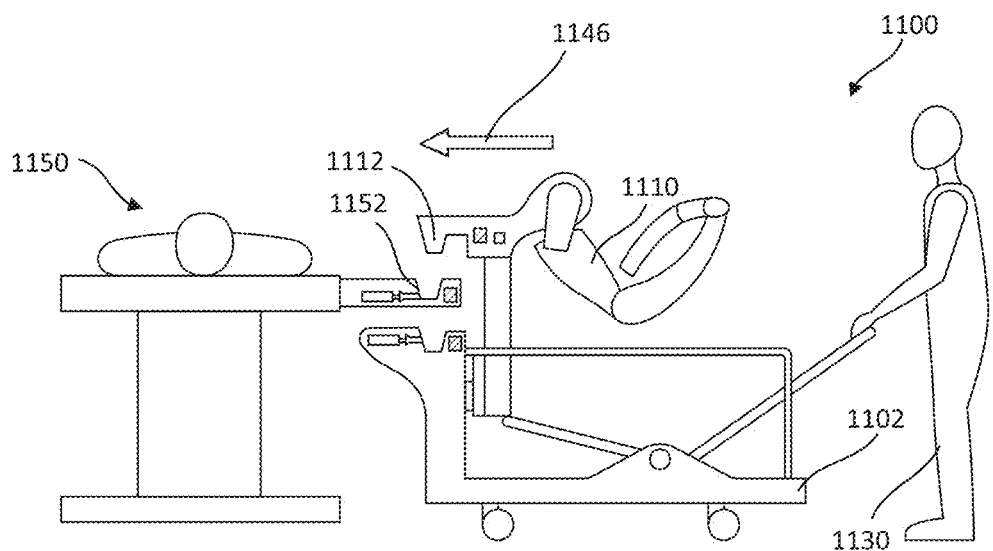

When stowed in the arm cart 1100, the robotic arm 1110 can be disposed at least partially within a perimeter defined by the arm cart 1100, such as is shown in FIG. 18. During movement of the arm cart 1100 on the support surface, the arm cart 1100 can protect the robotic arm 1110 from impact with objects. The arm cart 1100 can be pushed in a direction 1140 toward a surgical table, such as the surgical table 1150 shown in FIGS. 18-21. In FIG. 19, the robotic arm 1110 may be lifted out of the arm cart 1100. The user 1130 can lift the robotic arm 1110 in a direction 1144 by pressing or pushing down on the first segment 1134 of the actuating mechanism 1132 in a direction 1142. When the robotic arm 1110 is lifted in the direction 1144, the guide member 1128 slides upward with its motion restricted by the position of the follower 1126, which is disposed in the linear track defined by the guide member 1128. The actuating mechanism 1132 may be used to lift the robotic arm 1110 sufficiently high such that it vertically overshoots the coupling site 1152 of the surgical table 1150, as shown in FIG. 19. The arm cart 1100 may then be pushed in a direction 1146 such that the coupler 1112 of the robotic arm 1110 is positioned directly above the coupling site 1152 of the table 1150, as shown in FIG. 20. The robotic arm 1110 may then be lowered in a direction 1149 such that the coupler 1112 is placed over the coupling site 1152 and can be coupled to the coupling site 1152, as shown in FIG. 21. To lower the robotic arm 1110 in the direction 1149, the user 1130 can release the first segment 1134 such that the first segment 1134 moves upward in a direction 1148. The coupling site 1152 may include an electrical connector that is capable of connecting with an electrical connector disposed on the coupler 1112 and provide power and/or communicate with the robotic arm 1110. In some embodiments, the coupling site 1152 may have an identical structure as the attachment site 1124.

Although the arm cart 1100 is described as storing, deploying, and transferring only one robotic arm 1110, in some embodiments the arm cart 1100 can store, deploy, and transfer a second robotic arm similarly as described above with respect to the robotic arm 1110. For example, both the robotic arm 1110 and a second robotic arm can be loaded onto the arm cart 1100 prior to transfer of either robotic arm to a surgical table. The arm cart 1100 can include a second actuating mechanism and a second arm support, and the second robotic arm can be loaded into engagement with the second arm support. After transferring the robotic arm 1110 to a first coupling site of a surgical table as described above, the arm cart 1100 can be moved, with the second robotic arm in a stowed configuration, via the base 1104 to another location near the surgical table. The second arm support can then move the second robotic arm similarly as described above from the stowed configuration to the deployed configuration such that a coupler of the second robotic arm can be disposed in a proper position for engagement with a second coupling site associated with the surgical table. Once in the docking configuration and properly aligned with a coupling site of a surgical table, the second robotic arm can be transferred to the surgical table and the arm cart 1100 can be moved away from the surgical table.

In some embodiments, an arm cart with an attachment mechanism that attaches to a middle segment of a robotic arm may be used to mount a robotic arm to a surgical table. The attachment mechanism includes an arm interface or coupler that can grab onto (e.g., attach to) the robotic arm away from a proximal and distal end of the robotic arm. For example, the robotic arm may comprise a plurality of segments, which can be coupled together via joints that provide for translation along and/or rotation about one or more axes, such as is shown in FIGS. 1C and 1D. The arm interface of the attachment mechanism may attach to a segment of the robotic arm disposed between two middle joints (e.g., a first joint that is disposed at least one joint away from a distal end of the robotic arm and a second joint that is disposed at least one joint away from a proximal end of the robotic arm). By attaching to a middle segment of the robotic arm, the attachment mechanism may be capable of positioning the arm interface of the robotic arm such that it can be driven into a table adapter of the surgical table without making additional vertical adjustments to the robotic arm. For example, the attachment mechanism can position the arm interface of the robotic arm such that it can be slid onto the table adaptor of the surgical table without requiring a user to apply additional vertical motion.

The attachment mechanism also ensures that the arm is supported by either the arm cart or the table adapter while the arm is being transferred from the arm cart to the surgical table, minimizing the chances of the arm being dropped and damaged. The attachment mechanism may hold onto the arm while the arm is driven straight into the surgical table. Once the robotic arm is attached to the surgical table, the attachment mechanism may detach from the robotic arm and be moved away from the surgical table.

In some embodiments, the attachment mechanism may include an electrical connector that can connect to an electrical connector disposed on the robotic arm. The attachment mechanism may then use this electrical connection to supply power to and/or communicate with the robotic arm. For example, the attachment mechanism may supply power to the robotic arm such that the arm can be electrically powered and moved based on the position of the table adapter relative to the arm interface of the robotic arm. The attachment mechanism may use the multiple degrees of freedom of the arm provided by the joints of the arm to rotate and/or translate different segments of the arm to align the arm interface with the table adapter. In other embodiments, the arm may include an internal power supply that can be used to power and move the arm to account for any misalignment of the arm interface with the table adapter.

Figure 22:
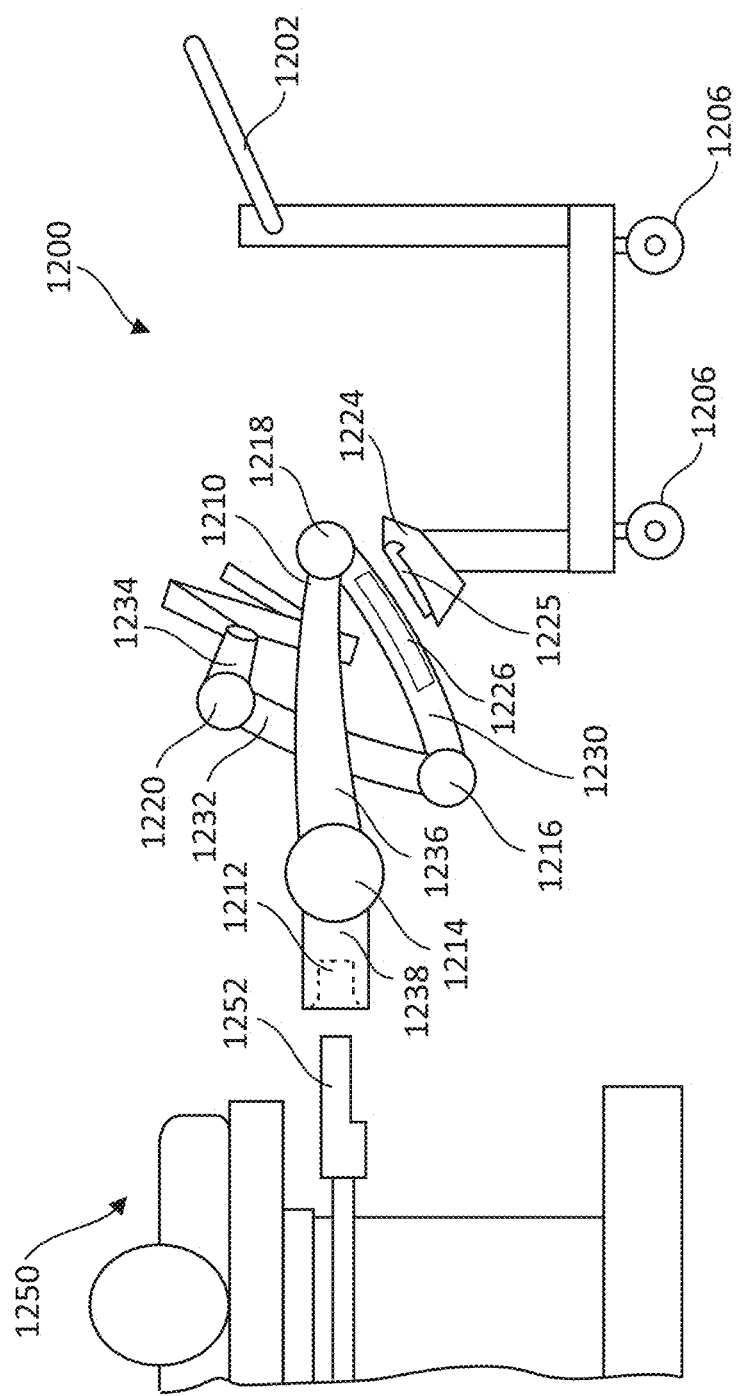
FIG. 22 is an illustration of an arm cart capable of coupling to a surgical arm at a location spaced from an end of the surgical arm, according to an embodiment.

FIG. 22 depicts an arm cart 1200 with an arm support 1224. The arm support 1224 may have an attachment mechanism 1225, which can attach to an attachment site 1226 disposed on a robotic arm 1210. The arm cart 1200 may also have a base that is freely moveable on a support surface, such as, for example, a floor, between a first location remote from a surgical table and a second location adjacent to the surgical table. For example, as depicted in FIG. 22, the arm cart 1200 is coupled to a number of wheels 1206 such that the arm cart 1200 is supported on the support surface. An operator can move the arm cart 1200 along the support surface by pushing or pulling on the push handle 1202.

As depicted in FIG. 22, the robotic arm 1210 is formed of multiple segments 1230, 1232, 1234, 1236, 1238 that are connected in serial to one another via a number of joints 1214, 1216, 1218, 1220. Specifically, a first segment 1238 disposed at a proximal end (e.g., mounting end) of the robotic arm 1210 can be connected to a second segment 1236 via a first joint 1214; the second segment 1236 can be connected to a third segment 1230 via a second joint 1216; the third segment 1230 can be connected to a fourth segment 1232 via a third joint 1218; the fourth segment 1232 can be connected to a fifth segment 1234 via a fourth joint 1220; and additional segments may be connected to each other via one or more additional joints. The joints 1214, 1216, 1218, 1220 can provide for translation along and/or rotation about one or more axes. The first segment 1238 disposed at the proximal end of the robotic arm 1210 may have a coupler 1212 that is configured to releasably couple to a coupling site 1252 of a surgical table 1250. Similar to other robotic arms described above, the robotic arm 1210 may be moved between various extended configurations for use during a surgical procedure and various folded or collapsed configurations for storage and/or transfer of the robotic arm 1210 to a surgical table.

The attachment site 1226 may be disposed on a middle segment of the robotic arm 1210, such as the third segment 1230. As shown in FIG. 22, the third segment 1230 is positioned at least two segments away from the proximal end of the robotic arm 1210—specifically, the first segment 1238 and the second segment 1236 separate the third segment 1230 from the proximal end of the robotic arm 1210. The middle segment 1230 is also positioned at least two segments (e.g., segments 1232, 1234) away from an opposite end of the robotic arm 1210. The attachment mechanism 1225 of the arm support 1224 may releasably couple to the third segment 1230 via the attachment site 1226. Because the attachment mechanism 1225 is coupled to a middle segment of the robotic arm 1210, the attachment mechanism 1225 allows the proximal end of the arm 1210 including the coupler 1212 to be adjusted via the joints and segments of the arm 1210 separating the middle segment from the proximal end of the arm 1210.

In some embodiments, the attachment mechanism 1225 and the attachment site 1226 may form an electrical connection through which the arm cart 1200 can supply power to and/or communicate with the robotic arm 1210. For example, the electrical connection between the attachment mechanism 1225 and the attachment site 1226 may allow a user to supply power to and move the robotic arm 1210 in order to align the coupler 1212 of the robotic arm 1210 with the coupling site 1252 of the surgical table 1250. In other embodiments, the robotic arm 1210 may have an internal power supply (e.g., a battery) that can be used to power the robotic arm 1210 to align the coupler 1212 with the coupling site 1252. In some embodiments, the robotic arm 1210 may also have a sensor disposed at or near its proximal end for detecting a location of the coupling site 1252 relative to the coupler 1212. Measurements from the sensor may be used to determine whether certain adjustments need to be made to the robotic arm 1210 in order to place the coupler 1212 into alignment with the coupling site 1252. The sensor may be configured to detect a receiver or other component and/or material disposed on the coupling site 1252. The sensor may function wirelessly or through a wired connection to a control panel on the arm cart 1200.

Once the coupler 1212 of the robotic arm 1210 is coupled to the coupling site 1252 of the surgical table 1250, the attachment mechanism 1225 may disengage or decouple from the attachment site 1226 and separate from the robotic arm 1210. The arm cart 1200 may then be freely moved away from the surgical table 1250 and the robotic arm 1210 (now coupled to the surgical table 1250). Although the arm cart 1200 is described as transferring only one robotic arm 1210, in some embodiments the arm cart 1200 can transfer a second robotic arm similarly as described above with respect to the robotic arm 1210. For example, the arm cart 1200 may include additional attachment mechanisms 1225 that can attach to one or more additional robotic arms.

Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

What is claimed is:

1. A cart for a surgical robotic arm having a coupler releasably coupleable to a coupling site on a surgical table, the cart comprising:
   a base freely movable between a first location remote from the surgical table and a second location adjacent to the surgical table; and
   an arm support coupled to the base and configured to be releasably coupled to the arm, the arm support including:
   a first member having one end coupled to a second member via a first swivel joint and another end coupled to the base;
   a third member having one end coupled to the second member via a second swivel joint and another end coupled to the arm;
   locking mechanisms configured to lock and unlock the first and second swivel joints,
   wherein the first and second swivel joints are configured to move the arm between a first position in which the coupler is not engageable with the coupling site and a second position in which the coupler is engageable with the coupling site when the base is at the second location.

2. The cart of claim 1, wherein the first swivel joint is configured to allow rotation about a first axis,
   wherein the second swivel joint is configured to allow rotation about a second axis different from the first axis.

3. The cart of claim 2, wherein the locking mechanisms include at least one release, the at least one release configured to be actuated to unlock at least one of the first swivel joint and the second swivel joint.

4. The cart of claim 3, wherein the second member is moveable relative to the first member when the first swivel joint is unlocked, and wherein the third member is moveable relative to the second member when the second swivel joint is unlocked.

5. The cart of claim 2, wherein the first member extends along the first axis, the second member extends along a third axis, and the third member extends along the second axis,
   wherein the third axis is orientated at a non-zero angle relative to the first and second axes.

6. The cart of claim 1, wherein the coupler includes an opening configured to slide onto the coupling site and engage with a mating feature disposed on the coupling site, the opening having a trapezoidal shape.

7. A method, comprising:
   moving a cart supporting a surgical robotic arm from a first location remote from a surgical table to a second location proximate to the surgical table, the surgical robotic arm including a coupler configured to releasably couple to a coupling site of the surgical table;
   manipulating an arm support of the cart to move the arm from a first position in which the coupler is not engageable with the coupling site to a second position in which the coupler is engageable with the coupling site, wherein manipulating the arm includes:
   unlocking a first swivel joint connecting a first member and a second member of the arm support;
   rotating the second member relative to the first member about a first axis;
   unlocking a second swivel joint connecting the second member and a third member of the arm support; and
   rotating the third member relative to the second member about a second axis; and
   releasably coupling the coupler to the coupling site.

8. The method of claim 7, wherein unlocking the first swivel joint includes actuating a first release of a locking mechanism from a first position to a second position, the locking mechanism configured to lock the first swivel joint when the first release is in the first position and to unlock the first swivel joint when the first release is in the second position.

9. The method of claim 8, wherein unlocking the second swivel joint includes actuating a second release of a locking mechanism from a first position to a second position, the locking mechanism configured to lock the second swivel joint when the second release is in the first position and to unlock the second swivel joint when the second release is in the second position.

10. The method of claim 7, wherein the cart further includes a base having a plurality of wheels, the plurality of wheels configured to lock to prevent movement of the cart and to unlock to permit the cart to move from the first location to the second location.

11. The method of claim 7, wherein releasably coupling the coupler to the coupling site includes sliding an opening defined by the coupler onto a mating feature disposed on the coupling site.

12. An apparatus, comprising:
    a coupler attached to a surgical robotic arm and configured to releasably couple to a coupling site on a surgical table, the coupler including:
    a first engagement member configured to releasably engage with an arm support of a cart;
    a second engagement member configured to releasably engage with a portion of the coupling site; and
    an actuator configured to engage and to disengage the first engagement member and the second engagement member; and
    the cart including:
    a base freely movable between a first location remote from the surgical table and a second location adjacent to the surgical table; and
    the arm support moveably coupled to the base and configured to releasably couple to the arm, the arm support including an attachment device defining an attachment area configured to receive the coupling site and the coupler,
    wherein the arm support is rotatable and translatable to permit movement of the attachment area such that the coupling site can be directed into the attachment area,
    wherein the attachment device includes one or more tapered surfaces configured to direct the coupling site into the attachment area.

13. The apparatus of claim 12, wherein the actuator is moveable from a first position to a second position, wherein the actuator engages the first engagement member to the arm support when the actuator is in the first position, wherein the actuator disengages the first engagement member from the arm support when the actuator is moved from the first position to the second position, wherein the actuator engages the second engagement member to the coupling site when the arm support is in the second position.

14. The apparatus of claim 13, wherein the first engagement member includes a wedge pin configured to be disposed in an opening of the arm support and the second engagement member includes a wedge pin configured to be disposed in an opening of the coupling site, wherein the first engagement member is disposed in the opening of the arm support when the actuator is in the first position, wherein the second engagement member is disposed in the opening of the coupling site when the actuator is in the second position.

15. The apparatus of claim 12, wherein the arm support further includes a lifting member moveable between a first position in which a portion of the lifting member is disposed above the attachment device and supports the arm and a second position in which the lifting member is disposed below the attachment device and separated from the arm.

16. The apparatus of claim 15, wherein the lifting member includes a wedge-shaped end configured to fit into an opening of the coupler when the lifting member is in the first position.

17. The apparatus of claim 12, wherein the cart further includes a linear rail, wherein the arm support is mounted on the linear rail such that the arm support is configured to translate along the linear rail.

* * * * *